United States Patent
Raheem et al.

(10) Patent No.: US 11,440,871 B2
(45) Date of Patent: Sep. 13, 2022

(54) ZUCLOMIPHENE SALTS AND CRYSTALLINE FORMS THEREOF

(71) Applicant: Apotex Inc., Toronto (CA)

(72) Inventors: Mohammed Abdul Raheem, Brantford (CA); Siva Ramarao Kakani, Brantford (CA); Minh T. N. Nguyen, Brantford (CA); Yajun Zhao, Brantford (CA); Stuart P. Green, Brantford (CA); Fabio E. S. Souza, Brantford (CA); Alexander J. Stirk, Brantford (CA); Fatemeh Mohammadpourmir, Brantford (CA)

(73) Assignee: Apotex Inc., Toronto (CA)

( * ) Notice: Subject to any disclaimer, the term of this patent is extended or adjusted under 35 U.S.C. 154(b) by 73 days.

(21) Appl. No.: 17/095,684

(22) Filed: Nov. 11, 2020

(65) Prior Publication Data

US 2021/0147338 A1    May 20, 2021

Related U.S. Application Data

(60) Provisional application No. 62/990,677, filed on Mar. 17, 2020, provisional application No. 62/935,123, filed on Nov. 14, 2019.

(51) Int. Cl.

| *C07C 213/08* | (2006.01) |
| *C07C 51/41* | (2006.01) |
| *C07C 15/24* | (2006.01) |
| *C07C 217/54* | (2006.01) |
| *C07C 59/265* | (2006.01) |

(52) U.S. Cl.
CPC ............ *C07C 213/08* (2013.01); *C07C 15/24* (2013.01); *C07C 51/41* (2013.01); *C07B 2200/13* (2013.01); *C07C 59/265* (2013.01); *C07C 217/54* (2013.01)

(58) Field of Classification Search
None
See application file for complete search history.

(56) References Cited

U.S. PATENT DOCUMENTS

| 2,914,563 A | 11/1959 | Mien et al. |
| 3,848,030 A | 11/1974 | Viterbo et al. |
| 9,428,442 B2 | 8/2016 | Serafini et al. |
| 9,913,815 B2 | 3/2018 | Steiner et al. |
| 9,914,696 B2 | 3/2018 | Podolski et al. |
| 2015/0202167 A1 | 7/2015 | Podolski et al. |

FOREIGN PATENT DOCUMENTS

| FR | 3082842 A1 | 12/2019 |
| GB | 1099093 | 1/1968 |
| WO | 2014031177 A1 | 2/2014 |
| WO | 2016014812 A1 | 1/2016 |
| WO | 2016106189 A1 | 6/2016 |

OTHER PUBLICATIONS

Al-Hassan, "Synthesis of Clomid Using Palladium-Catalyzed Cross-Coupling", Synthetic Communications, 1987, pp. 1787-1796, vol. 17:15.
Bernstein, "Polymorphism in Molecular Crystals", Oxford University Press, New York, 2002, 4 pages.
Crenshaw et al., "Synthesis of Trisubstituted Vinyl Chlorides", Journal of Organic Chemistry, 1983, pp. 2782-2784, vol. 48.
Dolginova et al., "Synthesis and Biological Study of the cis- and trans-Isomers of Clomiphene Citrate and Some Intermediates of Its Synthesis", Plenum Publishing Corporation, 1985, pp. 758-764.
Palopoli et al., "Substituted Aminoalkoxytriarylhaloethylenes", Journal of Medicinal Chemistry, 1967, pp. 84-86, vol. 10:1.
Porter, "Coating of Pharmaceutical Dosage Forms", Remington the Science and Practice of Pharmacy 21st Edition, Lippincott Williams & Wilkins, 2006, Chapter 46, pp. 929-938.
Rudnic et al., "Oral Solid Dosage Forms", Remington the Science and Practice of Pharmacy 21st Edition, Lippincott Williams & Wilkins, 2006, Chapter 45, pp. 889-928.
Stahl et al., "Handbook of Pharmaceutical Salts Properties, Selection, and Use", International Union of Pure and Applied Chemistry, 2002, 18 pages.
"Veru Announces Positive Top-Line Interim Data from Phase 2 Clinical Trial of Zuclomiphene to Treat Hot Flashes in Men with Prostate Cancer on Androgen Deprivation Therapy", Jan. 13, 2020, Retrieved from https://verupharma.com/news/, 5 pages.
Wilger et al., Nickel-Catalyzed Hydroarylation of Alkynes under Reductive Conditions with Aryl Bromides and Water, The Journal of Organic Chemistry, 2019, pp. 11612-11622, 84, ACS Publications, Birmingham.

*Primary Examiner* — Sudhakar Katakam
*Assistant Examiner* — Jennifer C Sawyer
(74) *Attorney, Agent, or Firm* — The Webb Law Firm

(57) ABSTRACT

The present invention provides zuclomiphene salts, zuclomiphene binaphthyl hydrogen phosphate salt (1-A)·(BPA) and zuclomiphene oxalate salt (1-A)·(OXL), crystalline forms thereof and processes for the preparation thereof.

9 Claims, 10 Drawing Sheets

ZUCLOMIPHENE SALTS AND CRYSTALLINE FORMS THEREOF

CROSS-REFERENCE TO RELATED APPLICATION

This application claims the benefit of U.S. Provisional Patent Applications No. 62/935,123, filed Nov. 14, 2019, and 62/990,677, filed Mar. 17, 2020, both of which disclosures are hereby incorporated by reference in their entireties.

TECHNICAL FIELD

The present invention is directed to zuclomiphene salts and crystalline forms thereof and to processes for the preparation thereof.

BACKGROUND

Clomid®, a drug initially approved by the United States Food and Drug Association in 1967 as an ovulatory stimulant, is an isomeric mixture of the citrate salts of cis-clomiphene (Z-clomiphene or 'zuclomiphene', (1-A)) and trans-clomiphene (E-clomiphene or 'enclomiphene', (1-B)) containing between 30% and 50% of the cis-isomer. Pure cis-isomer zuclomiphene, or (2-[4-[(Z)-2-chloro-1,2-diphenylethenyl]phenoxy]-N,N-diethylethanamine), in the form of the citrate salt, is currently under evaluation in clinical trials in the United States to treat hot flashes experienced by male patients with advanced prostate cancer undergoing androgen deprivation therapy (ADT).

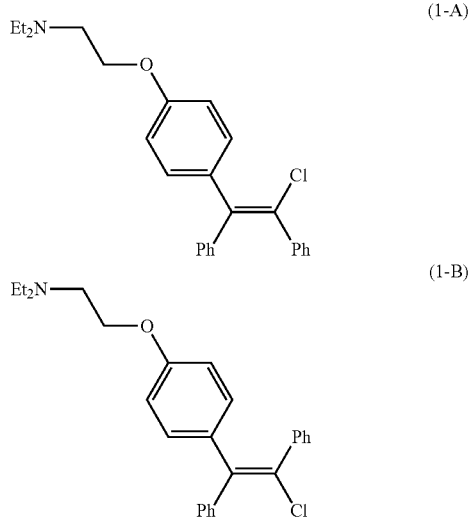

Until recently, interest in clomiphene isomers has largely focused on the E-isomer enclomiphene or mixtures thereof with zuclomiphene. Likewise, all reported synthetic methods to date, including for example Palopoli et al. *J. Med. Chem.* 1967, 10 (1), 84-6, WO 2014/031177 A1, and U.S. Pat. No. 9,428,442 B2 have afforded isomeric clomiphene mixtures which are typically comprised of 50-70% enclomiphene.

One method for retrieving pure zuclomiphene from an isomeric clomiphene mixture is by fractional crystallization of zuclomiphene free form or a salt thereof. For example, in U.S. Pat. No. 9,428,442 B2, it is reported that a mixture of clomiphene isomers can be separated by treating the mixture with racemic binaphthyl hydrogen phosphate ('BPA') in methanol. This procedure was originally described in U.S. Pat. No. 3,848,030 A, however the isomeric configurations were wrongly assigned therein and examples 31 and 32 have since been reported to afford the E- and Z-isomers, respectively, rather than the reverse configuration. Applying the correction to the separation procedure described in U.S. Pat. No. 3,848,030 A, the E-isomer enclomiphene separates out as the BPA salt which is collected by filtration and subsequently converted to the corresponding citrate salt. The Z-isomer zuclomiphene is recovered from the filtrate by addition of ammonia and extraction of the resulting free base into ether solvent followed by treatment of the extracts with an ethanolic citric acid solution to afford zuclomiphene as the citrate salt.

One major drawback of the process described in U.S. Pat. No. 3,848,030 A is that any impurities that are removed from the crystallized enclomiphene are likewise enriched in the filtrate where the desired zuclomiphene resides. As such, the purification burden is increased in the downstream citrate salt formation step, increasing the likelihood that more purification processing operations will be required.

Owing to the drawbacks of the existing processes, there remains a need for improved processes for the preparation of zuclomiphene, and salts thereof, that are more amenable to scale-up and use on a commercial scale.

SUMMARY OF THE INVENTION

The present invention provides salts of zuclomiphene and crystalline forms thereof, which are useful in the preparation of zuclomiphene (1-A) according to the processes of the invention, as depicted in Scheme 1.

As shown in Scheme 1, in the processes of the present invention, an initial isomer mixture of clomiphene isomers (or salts thereof), (1)·(HA)$_n$, is combined with binaphthyl hydrogen phosphate ('BPA') in a solvent to afford a solution comprising an isomer mixture of clomiphene binaphthyl hydrogen phosphate salts, (1)·(BPA). Crystallization and separation of a solid enriched in the enclomiphene binaphthyl hydrogen phosphate salt (1-B)·(BPA) from the solution affords a mother liquor enriched in the zuclomiphene binaphthyl hydrogen phosphate salt (1-A)·(BPA). In one embodiment, subsequent crystallization affords a solid from the mother liquor that is enriched in the zuclomiphene binaphthyl hydrogen phosphate salt (1-A)·(BPA. In an alternative embodiment, the binaphthyl hydrogen phosphate salt in the mother liquor is neutralized with base prior to addition of oxalic acid and recrystallization of a solid that is enriched in the zuclomiphene oxalate salt (1-A)·(OXL). In either embodiment, the salt may be further converted to an alternative salt thereof, such as zuclomiphene citrate salt or a free base thereof.

The present invention provides improved processes for the separation and isolation of clomiphene isomers from a mixture such as the mixture comprising 50-70% enclomiphene that is produced most commonly by reported procedures. The processes of the present invention are practical, simple, and industrially applicable and afford fractionation and recovery of zuclomiphene and enclomiphene isomers in high purity and good yield. Further provided are new zuclomiphene salts and crystalline forms thereof.

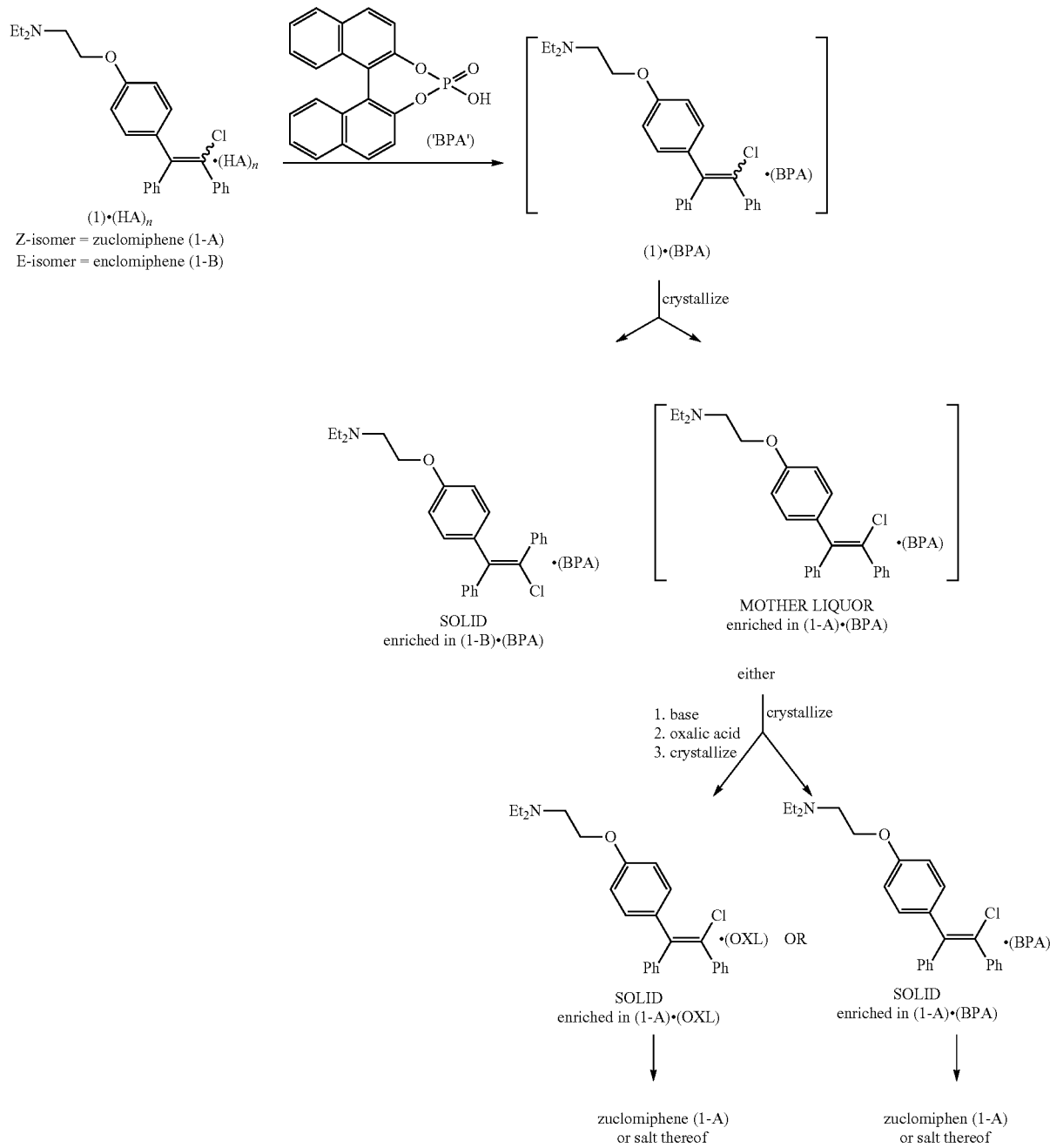
Scheme 1
wherein
n is 0, 0.5 or 1;
HA is an acid; and
the mixture (1)·(HA)$_n$ is enriched in the enclomiphene isomer in relation to the zuclomiphene isomer.
Accordingly, in a first aspect of the present invention, there is provided a process for the preparation of a solid that is isomerically enriched in zuclomiphene of Formula (1-A) relative to enclomiphene of Formula (1-B):
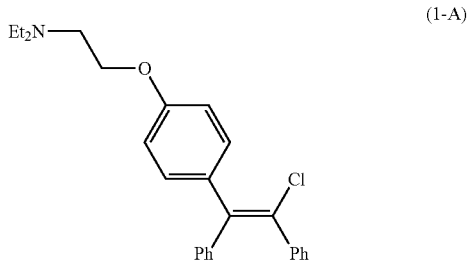
(1-A)

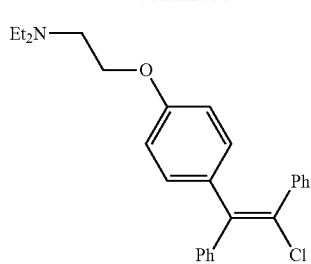

(1-B)

or a salt thereof, the process comprising:
(i) crystallizing and isolating a solid, from a mixture comprising enclomiphene binaphthyl hydrogen phosphate salt and zuclomiphene binaphthyl hydrogen phosphate salt in a solvent (S1), that is isomerically enriched in the enclomiphene binaphthyl hydrogen phosphate salt to afford a first solution;
and either:
(ii-a) crystallizing and isolating a solid from the first solution that is isomerically enriched in the zuclomiphene binaphthyl hydrogen phosphate salt; or
(ii-b)(a) treating the first solution with a base to liberate binaphthyl phosphate salt and removing it from the first solution to afford a second solution;
(b) treating the second solution with oxalic acid; and
(c) crystallizing and isolating a solid from the second solution that is isomerically enriched in the zuclomiphene oxalate salt;
wherein the mixture is enriched in enclomiphene binaphthyl hydrogen phosphate salt relative to zuclomiphene binaphthyl hydrogen phosphate salt.

In a preferred embodiment of the first aspect, step (i) comprises combining a composition comprising zuclomiphene and enclomiphene, or a composition comprising salts thereof, with binaphthyl hydrogen phosphate in a solvent (S1) and maintaining the mixture at a suitable temperature for a suitable time. Preferably, the composition comprises zuclomiphene citrate and enclomiphene citrate.

In another preferred embodiment of the first aspect, the solvent (S1) is selected from the group consisting of C1-C3 alcohols. Preferably, the solvent (S1) is methanol. In another preferred embodiment of the first aspect, the amount of solvent (S1) relative to the combined mass of enclomiphene binaphthyl hydrogen phosphate salt and zuclomiphene binaphthyl hydrogen phosphate salt is in the range of about 8 volumes to about 16 volumes. In a further preferred embodiment of the first aspect, the suitable temperature is in the range of about 25° C. to about 60° C. In another preferred embodiment of the first aspect, the suitable time is in the range of about 2 hours to about 10 hours.

In a further preferred embodiment of the first aspect, the process comprises step (ii)(a) and any one or more of the following steps: 1. stirring the first solution for a suitable time; 2. cooling the first solution; 3. adding a solvent (S2) to the first solution; 4. increasing the concentration of the first solution; and 5. seeding the first solution. Preferably, the suitable time is in the range of about 2 hours to about 20 hours. Preferably, step 2. comprises cooling the first solution to a temperature in the range of about 0° C. to about 5° C. Preferably, the solvent (S2) in step 3. is methyl t-butyl ether. Preferably, step 4. comprises evaporation of the first solution to a reduced volume.

In a further preferred embodiment of the first aspect, the isomeric ratio of zuclomiphene:enclomiphene in the mixture is in the range of about 20:80 to about 45:55. Preferably, the isomeric ratio of zuclomiphene:enclomiphene in the mixture is in the range of about 45:55 to about 35:65. In another preferred embodiment, the isomeric ratio of zuclomiphene:enclomiphene in the solid that is isolated in step (ii)(a) is in the range of about 95:5 to about 100:0. Preferably, the isomeric ratio of zuclomiphene:enclomiphene in the solid that is isolated in step (ii)(a) is in the range of about 97:3 to about 100:0.

In a further preferred embodiment of the first aspect, the process comprises steps (ii-b)(a), (ii-b)(b), and (ii-b)(c). In another preferred embodiment of the first aspect, the base is selected from the group consisting of potassium carbonate, sodium carbonate, potassium hydroxide, and sodium hydroxide, preferably the base is solid potassium carbonate. In a further preferred embodiment of the first aspect, solid potassium binaphthyl phosphate salt is generated and is removed from the first solution by filtration. Preferably, solvent (S1) is methanol and step (ii-b)(a) comprises replacing a portion of the methanol with ethyl acetate and water such that the solvent composition comprises, with respect to ethyl acetate, about 10-15 mole % water and less than about 20 mole % methanol, prior to filtration.

In a further preferred embodiment of the first aspect, the zuclomiphene binaphthyl hydrogen phosphate salt or the zuclomiphene oxalate salt that is isolated is further converted to zuclomiphene citrate salt.

In a second aspect of the present invention, there is provided a process for the preparation of a solid that is isomerically enriched in zuclomiphene of Formula (1-A) relative to enclomiphene of Formula (1-B):

(1-A)

(1-B)

or a salt thereof, the process comprising:
(i) providing a first solution of zuclomiphene binaphthyl hydrogen phosphate salt in a solvent (S5), wherein the salt has an initial isomeric purity of at least about 75% (Z);
and either:
(ii-a) crystallizing and isolating a solid from the first solution that is isomerically enriched in the zuclomiphene binaphthyl hydrogen phosphate salt; or
(ii-b)(a) treating the first solution with a base to liberate binaphthyl phosphate salt and removing it from the first solution to afford a second solution;

(b) treating the second solution with oxalic acid; and
(c) crystallizing and isolating a solid from the second solution that is isomerically enriched in the zuclomiphene oxalate salt.

In a preferred embodiment of the second aspect, the solvent (S5) is selected from the group consisting of C1-C3 alcohols. Preferably, the solvent (S5) is methanol.

In a further preferred embodiment of the second aspect, the process comprises step (ii)(a) and any one or more of the following steps: 1. stirring the first solution for a suitable time; 2. cooling the first solution; 3. adding a solvent (S6) to the first solution; 4. increasing the concentration of the first solution; and 5. seeding the first solution. Preferably, the suitable time is in the range of about 2 hours to about 20 hours. Preferably, step 2. comprises cooling the first solution to a temperature in the range of about 0° C. to about 5° C. Preferably, the solvent (S6) in step 3. is methyl t-butyl ether. Preferably, step 4. comprises evaporation of the first solution to a reduced volume.

In a further preferred embodiment of the second aspect, the process comprises steps (ii-b)(a), (ii-b)(b), and (ii-b)(c). In another preferred embodiment of the second aspect, the base is selected from the group consisting of potassium carbonate, sodium carbonate, potassium hydroxide, and sodium hydroxide, preferably the base is solid potassium carbonate. In a further preferred embodiment of the second aspect, solid potassium binaphthyl phosphate salt is generated and is removed from the first solution by filtration. Preferably, solvent (S5) is methanol and step (ii-b)(a) comprises replacing a portion of the methanol with ethyl acetate and water such that the solvent composition comprises, with respect to ethyl acetate, about 10-15 mole % water and less than about 20 mole % methanol, prior to filtration.

In another preferred embodiment of the second aspect, the initial isomeric purity of the zuclomiphene binaphthyl hydrogen phosphate salt is at least about 85% (Z). In a further preferred embodiment of the second aspect, the isomeric purity of the zuclomiphene binaphthyl hydrogen phosphate salt that is isolated is at least about 97% (Z).

In another preferred embodiment of the second aspect, the zuclomiphene binaphthyl hydrogen phosphate salt that is isolated is further converted to zuclomiphene free base or zuclomiphene citrate salt, preferably it is further converted to a citrate salt.

In a third aspect of the present invention, there is provided a crystalline zuclomiphene binaphthyl hydrogen phosphate salt. In a preferred embodiment of the third aspect, the crystalline salt is APO-I, characterized by a PXRD diffractogram comprising peaks, expressed in degrees 2θ (±0.2°), at 9.2°, 10.5° and 12.0°. In a further preferred embodiment of the third aspect, the PXRD diffractogram further comprises at least three peaks, expressed in degrees 2θ (±0.2°), selected from the group consisting of: 4.0°, 7.9°, 11.0°, 13.0°, 16.0°, 17.0° and 19.2°. In another preferred embodiment of the third aspect, the PXRD diffractogram further comprises peaks, expressed in degrees 2θ (±0.2°), at 4.0°, 7.9°, 11.0°, 13.0°, 16.0°, 17.0° and 19.2°. Preferably, the crystalline salt of the third aspect provides a PXRD diffractogram comprising peaks in substantially the same positions (±0.2° 2θ) as those shown in FIG. 1. In a further preferred embodiment of the third aspect, the crystalline salt is characterized by a DSC thermogram comprising an endothermic peak with a peak onset of about 214° C. and a peak maximum of about 216° C. Preferably, the crystalline salt of the third aspect is characterized by a DSC thermogram that is substantially the same in appearance as the DSC thermogram provided in FIG. 2.

In a fourth aspect of the present invention, there is provided a crystalline zuclomiphene oxalate salt. In a preferred embodiment of the fourth aspect, the crystalline salt is APO-I, characterized by a PXRD diffractogram comprising peaks, expressed in degrees 2θ (±0.2°), at 6.5°, 13.1° and 14.5°. In a further preferred embodiment of the fourth aspect, the PXRD diffractogram of APO-I further comprises at least three peaks, expressed in degrees 2θ (±0.2°), selected from the group consisting of: 11.1°, 12.5°, 16.4°, 17.7°, 18.8°, 19.6°, 20.5°, 21.4°, 22.4° and 25.2°. In another preferred embodiment of the fourth aspect, the PXRD diffractogram of APO-I further comprises peaks, expressed in degrees 2θ (±0.2°), at 11.1°, 12.5°, 16.4°, 17.7°, 18.8°, 19.6°, 20.5°, 21.4°, 22.4° and 25.2°. Preferably, the PXRD diffractogram of APO-I of the fourth aspect comprises peaks in substantially the same positions (±0.2° 2θ) as those shown in FIG. 3. In a further preferred embodiment of the fourth aspect, APO-I is characterized by a DSC thermogram having a first endothermic peak with a peak onset at about 137° C. and a peak maximum at about 139° C. and a second endothermic peak with a peak onset at about 163° C. and a peak maximum at about 164° C. Preferably, APO-I of the fourth aspect is characterized by a DSC thermogram that is substantially the same in appearance as the DSC thermogram provided in FIG. 4.

In a preferred embodiment of the fourth aspect, the crystalline salt is APO-II, characterized by a PXRD diffractogram comprising peaks, expressed in degrees 2θ (±0.2°), at 5.3°, 10.6° and 14.0°. In a further preferred embodiment of the fourth aspect, the PXRD diffractogram of APO-II further comprises at least three peaks, expressed in degrees 2θ (±0.2°), selected from the group consisting of: 10.2°, 12.0°, 13.4°, 14.7°, 15.9°, 16.3°, 18.6°, 20.0°, 20.6° and 22.7°. In another preferred embodiment of the fourth aspect, the PXRD diffractogram of APO-II further comprises peaks, expressed in degrees 2θ (±0.2°), at 10.2°, 12.0°, 13.4°, 14.7°, 15.9°, 16.3°, 18.6°, 20.0°, 20.6° and 22.7°. Preferably, the PXRD diffractogram of APO-II of the fourth aspect comprises peaks in substantially the same positions (±0.2° 2θ) as those shown in FIG. 5. In a further preferred embodiment of the fourth aspect, APO-II is characterized by a DSC thermogram having a first endothermic peak with a peak onset at about 163° C. and a peak maximum at about 164° C. Preferably, APO-II of the fourth aspect is characterized by a DSC thermogram that is substantially the same in appearance as the DSC thermogram provided in FIG. 6.

In a preferred embodiment of the fourth aspect, the crystalline salt is APO-III, characterized by a PXRD diffractogram comprising peaks, expressed in degrees 2θ (±0.2°), at 5.2°, 17.0° and 18.9°. In a further preferred embodiment of the fourth aspect, the PXRD diffractogram of APO-III further comprises at least three peaks, expressed in degrees 2θ (±0.2°), selected from the group consisting of: 9.8°, 10.2°, 10.5°, 12.3°, 14.1°, 17.7°, 19.7°, 20.7°, 23.0° and 25.6°. In another preferred embodiment of the fourth aspect, the PXRD diffractogram of APO-III further comprises peaks, expressed in degrees 2θ (±0.2°), at 9.8°, 10.2°, 10.5°, 12.3°, 14.1°, 17.7°, 19.7°, 20.7°, 23.0° and 25.6°. Preferably, the PXRD diffractogram of APO-III of the fourth aspect comprises peaks in substantially the same positions (±0.2° 2θ) as those shown in FIG. 7. In a further preferred embodiment of the fourth aspect, APO-III is characterized by a DSC thermogram having a first endothermic peak with a peak onset at about 105° C. and a peak maximum at about 106° C. Preferably, APO-III of the fourth aspect is characterized by a DSC thermogram that is substantially the same in appearance as the DSC thermogram provided in FIG. 8.

In a preferred embodiment of the fourth aspect, the crystalline salt is APO-IV, characterized by a PXRD diffractogram comprising peaks, expressed in degrees 2θ (±0.2°), at 6.8°, 10.2° and 18.5°. In a further preferred embodiment of the fourth aspect, the PXRD diffractogram of APO-IV further comprises at least three peaks, expressed in degrees 2θ (±0.2°), selected from the group consisting of: 12.8°, 13.7°, 15.1°, 16.0°, 16.8°, 19.4°, 20.3°, 22.6°, 23.3° and 24.7°. In another preferred embodiment of the fourth aspect, the PXRD diffractogram of APO-IV further comprises peaks, expressed in degrees 2θ (±0.2°), at 12.8°, 13.7°, 15.1°, 16.0°, 16.8°, 19.4°, 20.3°, 22.6°, 23.3° and 24.7°. Preferably, the PXRD diffractogram of APO-IV of the fourth aspect comprises peaks in substantially the same positions (±0.2° 2θ) as those shown in FIG. 9. In a further preferred embodiment of the fourth aspect, APO-IV is characterized by a DSC thermogram having a first endothermic peak with a peak onset at about 150° C. and a peak maximum at about 151° C. Preferably, APO-IV of the fourth aspect is characterized by a DSC thermogram that is substantially the same in appearance as the DSC thermogram provided in FIG. 10.

BRIEF DESCRIPTION OF THE DRAWINGS

Embodiments of the present invention are described, by way of example only, with reference to the attached Figures.

DETAILED DESCRIPTION

Figure 1:
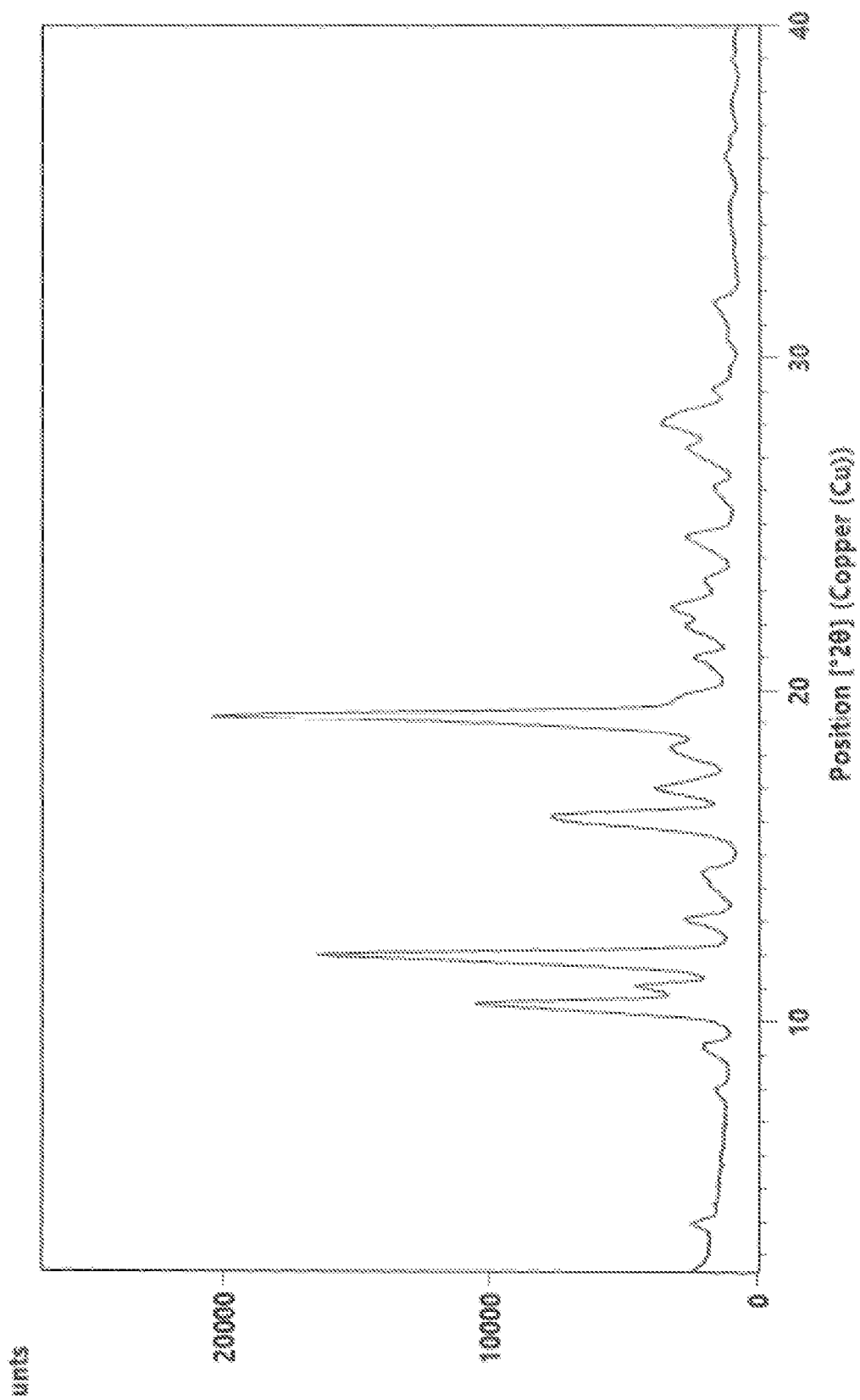
FIG. 1 is a representative PXRD diffractogram of zuclomiphene binaphthyl hydrogen phosphate Form APO-I as prepared in Example 2.

As shown in Scheme 1, in the processes of the present invention, an initial isomer mixture of enclomiphene and zuclomiphene isomers (or salts thereof), (1)·(HA)$_n$, is combined with binaphthyl hydrogen phosphate ('BPA') in a solvent to afford a solution comprising an isomer mixture of enclomiphene and zuclomiphene binaphthyl hydrogen phosphate salts (1)·(BPA). Crystallization and separation of a solid enriched in the enclomiphene binaphthyl hydrogen phosphate salt (1-B)·(BPA) from the solution affords a mother liquor enriched in the zuclomiphene binaphthyl hydrogen phosphate salt (1-A)·(BPA). In one embodiment, subsequent crystallization affords a solid from the mother liquor that is enriched in the zuclomiphene binaphthyl hydrogen phosphate salt (1-A)·(BPA). Alternatively, the binaphthyl hydrogen phosphate salt in the mother liquor is neutralized with base prior to addition of oxalic acid and recrystallization of a solid that is enriched in the zuclomiphene oxalate salt (1-A)·(OXL). In either embodiment, the salt may be further converted to an alternative salt thereof, such as zuclomiphene citrate salt or a free base thereof.

The present invention provides improved processes for the separation and isolation of clomiphene isomers from a mixture such as the mixture of isomers comprising from 50-70% of enclomiphene that is most commonly produced by reported procedures. Surprisingly, in the processes of the present invention, the binaphthyl hydrogen phosphate salt of zuclomiphene can be directly crystallized in high purity from a solution that is enriched in the zuclomiphene binaphthyl hydrogen phosphate salt relative to the corresponding enclomiphene salt. Alternatively, rather than directly crystallizing the zuclomiphene binaphthyl hydrogen phosphate salt, it is neutralized, oxalic acid is added, and the corresponding zuclomiphene oxalate salt is crystallized in high purity from the solution. In embodiments of the present invention, the isomeric purity of the crystallized zuclomiphene binaphthyl hydrogen phosphate salt or zuclomiphene oxalate salt is higher than that of the zuclomiphene citrate salt that is isolated by the method of separating clomiphene isomers that is reported in U.S. Pat. No. 3,848,030 A.

The processes of the present invention are practical, simple, and industrially applicable and afford fractionation and recovery of zuclomiphene and enclomiphene isomers in high purity and good yield. Further provided is crystalline zuclomiphene binaphthyl hydrogen phosphate salt and a crystalline form thereof, as well as crystalline zuclomiphene oxalate salt and crystalline forms thereof.

As used herein, the terms "BPA" and "binaphthyl hydrogen phosphate" refers to racemic binaphthyl hydrogen phosphate ((+/−)-1,1'-binaphthyl-2,2'-diyl hydrogen phosphate).

As used herein, the term "citrate" refers to the dihydrogen citrate ion that is the counterion in clomiphene citrate.

As used herein, the term "alkyl", means, unless otherwise stated a straight chain, branched chain, or non-aromatic cyclic hydrocarbon radical having the number of carbon atoms designated. When there is no indication of the number of carbon atoms in the alkyl, it is meant, unless otherwise indicated by context, that there are from 1 to 6 carbon atoms. Examples of preferred alkyl groups include methyl, ethyl, n-propyl, iso-propyl, n-butyl, t-butyl, iso-butyl and sec-butyl.

As used herein, "room temperature" generally refers to a temperature of 20-25° C.

As used herein, the term "volumes" refers to the parts of solvent or liquids by volume (mL) with respect to the weight of solute (g). For example, when a reaction is conducted using 1 g of starting material and 100 mL of solvent, it is said that 100 volumes of solvent are used.

As used herein, the term "isomeric ratio" refers to the relative mole ratio of the two isomers enclomiphene and zuclomiphene or to the relative mole ratio of salts thereof.

As used herein, the term "isomeric purity" refers to the amount of the subject enclomiphene or zuclomiphene (or a salt thereof) relative to the total amount of enclomiphene and zuclomiphene (or a salt thereof), expressed as a percentage.

As used herein, the term "substantially isomerically pure" refers to enclomiphene or zuclomiphene (or a salt thereof) containing less than about 1 mol % of its respective isomer (or a salt thereof), preferably less than about 0.5 mol %, most preferably, less than about 0.2 mol %.

As used herein, the term "about" means "close to", and that variation from the exact value that follows the term is within amounts that a person of skill in the art would understand to be reasonable. For example, when the term "about" is used with respect to temperature, a variation of ±5° C. is generally acceptable when carrying out the processes of the present invention. When used with respect to mole equivalents, a variation of ±0.1 moles is generally acceptable.

As used herein, the term 'crystalline form' refers to a substance with a particular arrangement of molecular components in its crystal lattice, and which may be identified by physical characterization methods such as PXRD.

Depending on the manner in which the crystalline forms of the present invention are prepared, and the methodology and instrument used for PXRD analysis, the intensity of a given peak observed in a PXRD diffractogram of the crystalline form may vary when compared to the same peak in the representative PXRD diffractograms provided in FIGS. 1, 3, 5, 7 and 9. Thus, differences in relative peak intensities between peaks in a PXRD diffractogram for a given crystalline form may be observed when compared to the relative peak intensities of the peaks in the representative PXRD diffractograms of FIGS. 1, 3, 5, 7 and 9. Any such differences may be due, in part, to the preferred orientation of the sample and its deviation from the ideal random sample orientation, the preparation of the sample for analysis, and the methodology applied for the analysis. Such variations are known and understood by a person of skill in the art, and any such variations do not depart from the invention disclosed herein.

In addition to the differences in relative peak intensities that may be observed in comparison to the representative PXRD diffractograms provided in FIGS. 1, 3, 5, 7 and 9, it is understood that individual peak positions may vary between ±0.2° 2θ from the values observed in the representative PXRD diffractograms provided in FIGS. 1, 3, 5, 7 and 9 for the crystalline forms of the invention, or listed in Tables 1 to 5. Such variations are known and understood by a person of skill in the art, and any such variations do not depart from the invention disclosed herein.

Further, depending on the instrument used for X-ray analysis and its calibration, uniform offsets in the peak position of each peak in a PXRD diffractogram of greater that 0.2° 2θ may be observed when compared to the representative PXRD diffractograms provided in FIGS. 1, 3, 5, 7 and 9. Thus, PXRD diffractograms of the crystalline form of the present invention may, in some circumstances, display the same relative peak positions as observed in the representative PXRD diffractograms provided in FIGS. 1, 3, 5, 7 and 9, with the exception that each peak is offset in the same direction, and by about the same amount, such that the overall PXRD diffractogram is substantially the same in appearance as the PXRD diffractograms of FIGS. 1, 3, 5, 7 and 9, with the exception of the uniform offset in peak positions. The observation of any such uniform peak shift in a PXRD diffractogram does not depart from the invention disclosed herein given that the relative peak positions of the individual peaks within the PXRD diffractogram remain consistent with the relative peak positions observed in the PXRD diffractograms of FIGS. 1, 3, 5, 7 and 9.

Depending on the manner in which the crystalline forms are prepared, the methodology and instrument used for DSC analysis, it is understood that peaks corresponding with thermal events in a DSC thermogram may vary between ±2° C. from the values observed in the representative DSC thermograms provided in FIGS. 2, 4, 6, 8 and 10 and described herein. Such variations are known and understood by a person of skill in the art, and any such variations do not depart from the invention disclosed herein.

When describing the embodiments of the present invention there may be a common variance to a given temperature or time that would be understood or expected by the person skilled in the art to provide substantially the same result. For example, when reference is made to a particular temperature, it is to be understood by the person skilled in the art that there is an allowable variance of ±5° C. associated with that temperature. When reference is made to a particular time, it is to be understood that there is an allowable variance of ±10 minutes when the time is one or two hours, and ±1 hour when longer periods of time are referenced.

In a first embodiment of the present invention, there is provided a process for the preparation of a solid that is isomerically enriched in zuclomiphene of Formula (1-A) relative to enclomiphene of Formula (1-B):

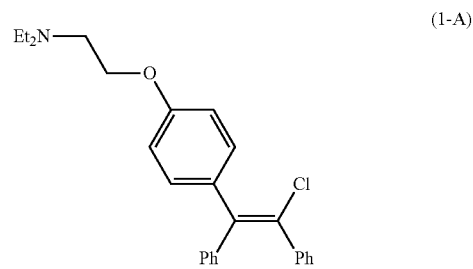

(1-A)

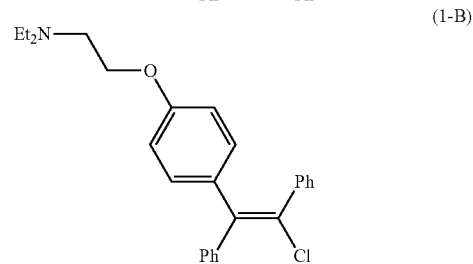

(1-B)

or a salt thereof, the process comprising:
(i) crystallizing and isolating a solid, from a mixture comprising enclomiphene binaphthyl hydrogen phosphate salt and zuclomiphene binaphthyl hydrogen phosphate salt in a solvent (S1), that is isomerically enriched in the enclomiphene binaphthyl hydrogen phosphate salt to afford a first solution;
and either:
(ii-a) crystallizing and isolating a solid from the first solution that is isomerically enriched in the zuclomiphene binaphthyl hydrogen phosphate salt; or
(ii-b)(a) treating the first solution with a base to liberate binaphthyl phosphate salt and removing it from the first solution to afford a second solution;
(b) treating the second solution with oxalic acid; and
(c) crystallizing and isolating a solid from the second solution that is isomerically enriched in the zuclomiphene oxalate salt;
wherein the mixture is enriched in enclomiphene binaphthyl hydrogen phosphate salt relative to zuclomiphene binaphthyl hydrogen phosphate salt.

The solvent (S1) may be selected from the group consisting of C1-C3 alcohols and mixtures thereof with an alkyl ether. Preferably, the solvent (S1) is methanol or a mixture of methanol and methyl t-butyl ether.

A suitable volume of the solvent (S1) is used to promote fluidity and stir-ability of the mixture. As described in Comparative Example 1, reproduction of conditions analogous to those of Example 31 of U.S. Pat. No. 3,848,030 A (wherein clomiphene citrate is treated with binaphthyl hydrogen phosphate in methanol) affords a thick, paste-like and intractable suspension. Preferably, the suitable volume of solvent (S1) in relation to the combined mass of enclomiphene binaphthyl hydrogen phosphate salt and zuclomiphene binaphthyl hydrogen phosphate salt is in the range of about 8 volumes to about 16 volumes. More preferably, the volume of solvent (S1) is in the range of about 10 volumes to about 12 volumes, most preferably it is about 12 volumes. When appropriate, the combined mass of enclomiphene binaphthyl hydrogen phosphate salt and zuclomiphene binaphthyl hydrogen phosphate salt is calculated by assuming complete conversion from the input source of the clomiphene isomer mixture, such as the citrate salt.

In an embodiment of step (i), the crystallization may comprise combining a composition comprising binaphthyl hydrogen phosphate salts of enclomiphene and zuclomiphene with a solvent (S1) and applying suitable crystallization techniques such as cooling, concentration, seeding and/or addition of a suitable solvent.

In another embodiment of step (i), the crystallization involves a reactive crystallization comprising combining a composition comprising zuclomiphene and enclomiphene free base forms, or a composition comprising salts thereof, with binaphthyl hydrogen phosphate in a solvent (S1) followed by maintaining the resulting mixture at a suitable temperature for a suitable time to afford a suspension. A suitable salt is derived from an acid (HA) which may bear one or more acidic protons selected from the group consisting of D,L-aspartic acid, cyclamic acid, fumaric acid, L-glutamic acid, hippuric acid, L-malic acid, malonic acid, nicotinic acid, di-p-toluoyl-D-tartaric acid, saccharin, D-tartaric acid, and citric acid. Preferably, the acid (HA) is citric acid and the composition comprises zuclomiphene citrate and enclomiphene citrate wherein the stoichiometry of clomiphene isomer to citrate counter-ion is about 1:1.

In this reactive crystallization embodiment, the suitable temperature is in the range of about 25° C. to about 60° C. Preferably, the suitable time is in the range of about 2 hours to about 8 hours. Most preferably, the mixture is maintained at a first temperature in the range of about 50° C. to about 60° C. for a time in the range of about 2 hours to about 4 hours, followed by a second maintenance period at a temperature in the range of about 25° C. to about 35° C. for about 2 hours to about 4 hours.

The mixture used in step (i) is enriched in the enclomiphene isomer relative to the zuclomiphene isomer and the isomeric ratio of zuclomiphene:enclomiphene in the mixture is in the range of about 20:80 to about 45:55, most preferably, the ratio is in the range of about 45:55 to about 35:65.

Separation of the solid in step (i) may be accomplished by any suitable means including decantation, centrifugation, or filtration, preferably filtration.

The solid that is isolated in step (i) is isomerically enriched in the enclomiphene binaphthyl hydrogen phosphate salt in relation to the zuclomiphene binaphthyl hydrogen phosphate salt. Preferably, the isomeric ratio of enclomiphene:zuclomiphene in this isolated solid is in the range of about 90:10 to about 100:0, more preferably it is in the range of about 95:5 to about 100:0, even more preferably, it is in the range of about 97:3 to about 100:0. Most preferably, the solid that is isolated is substantially isomerically pure enclomiphene binaphthyl hydrogen phosphate salt.

The molar recovery of the enclomiphene binaphthyl hydrogen phosphate salt from the available enclomiphene is preferably greater than about 80%, more preferably greater than about 85%, most preferably greater than about 90%.

In the embodiment proceeding through step (ii-a), crystallizing a solid may comprise any one or more of the following steps: stirring and maintaining the first solution for a suitable time; cooling the first solution; adding a solvent (S2) to the first solution; increasing the concentration of the first solution; and seeding the first solution. Preferably, the first solution is stirred for a suitable time to encourage crystallization, preferably for a suitable time in the range of about 2 hours to about 20 hours, most preferably the suitable time is in the range of about 4 hours to about 8 hours. Preferably, the first solution is concentrated to a lower volume than the initial volume of the first solution, preferably it is concentrated to a volume, in relation to the combined mass of enclomiphene binaphthyl hydrogen phosphate salt and zuclomiphene binaphthyl hydrogen phosphate salt (which can be calculated as described above) in the range of about 3 volumes to about 5 volumes. Preferably, the first solution is treated with a solvent (S2) to lower the solubility of the salt that is preferably an alkyl ether. More preferably, the solvent (S2) is selected from the group consisting of methyl t-butyl ether, tetrahydrofuran, and 2-methyltetrahydrofuran. Most preferably, the solvent (S2) is methyl t-butyl ether. Preferably, the first solution is cooled to a temperature in the range of about 0° C. to about 10° C., most preferably the temperature is in the range of about 0° C. to about 5° C.

Isolation of the solid in step (ii-a) may be accomplished by any suitable means including decantation, centrifugation, or filtration, preferably filtration.

The solid that is isolated in step (ii-a) is isomerically enriched in the zuclomiphene binaphthyl hydrogen phosphate salt in relation to the enclomiphene binaphthyl hydrogen phosphate salt. Preferably, the isomeric ratio of zuclomiphene:enclomiphene in this isolated solid is in the range of about 90:10 to about 100:0, more preferably it is in the range of about 95:5 to about 100:0, even more preferably, it is in the range of about 97:3 to about 100:0. Most preferably, the solid that is isolated is substantially isomerically pure zuclomiphene binaphthyl hydrogen phosphate salt.

Preferably, the solid that is isolated in step (ii-a) is a new crystalline salt of zuclomiphene, crystalline zuclomiphene binaphthyl hydrogen phosphate, and is most preferably crystalline zuclomiphene binaphthyl hydrogen phosphate Form APO-I.

The solid that is isolated in step (ii-a) may be further converted to an alternative zuclomiphene salt thereof or to zuclomiphene free base. Preferably, the solid is further converted to zuclomiphene citrate salt by a process comprising: i) combining zuclomiphene binaphthyl hydrogen phosphate salt with a solid base, a solvent (S3) and a minimum amount of water sufficient to afford a third suspension; ii) separating the solid from the third suspension to afford a solution of zuclomiphene free base; and iii) treating the zuclomiphene free base with citric acid to afford zuclomiphene citrate salt. In this process, the base may be selected from the group consisting of potassium carbonate, sodium carbonate, potassium hydroxide, and sodium hydroxide. Preferably the base is potassium carbonate. The solvent (S3) may be selected from the group consisting of esters, ethers, and ketones. Preferably, the solvent (S3) may be selected from the group consisting of ethyl acetate, methyl t-butyl ether, and methyl ethyl ketone. Most preferably, the solvent (S3) is ethyl acetate. Conveniently, the solid that is isolated from the third suspension can be acidified to regenerate the binaphthyl hydrogen phosphate which may be recycled if desired.

In the embodiment proceeding through steps (ii-b)(a), (ii-b)(b), and (ii-b)(c), the first solution, which corresponds to the mother liquor of the first crystallization in step (i), is treated with base to liberate the free base forms of enclomiphene and zuclomiphene from the binaphthyl hydrogen phosphate and citric acid. Preferably, a portion of the solvent (S1) comprising the first solution is replaced with solvent (S4) that is selected from the group consisting of esters, ethers, and ketones. Preferably, the solvent (S4) is selected from the group consisting of ethyl acetate, methyl ethyl ketone, acetone, and mixtures thereof. Most preferably, the solvent (S4) is ethyl acetate or a mixture thereof with acetone. Preferably, the suitable volume of solvent (S4) in relation to the combined mass of enclomiphene binaphthyl hydrogen phosphate salt and zuclomiphene binaphthyl hydrogen phosphate salt (which can be calculated as described above) is in the range of about 3 volumes to about 5 volumes.

In a preferred embodiment of step (ii-b)(a), the binaphthyl hydrogen phosphate is removed from the first solution by filtration of an insoluble binaphthyl phosphate salt formed by treatment of the first solution with the base. The base may be selected from the group consisting of potassium carbonate, sodium carbonate, potassium hydroxide, and sodium hydroxide. Preferably, the base is potassium carbonate which is added as a solid, along with a minimum amount of water, to the first solution comprising solvent (S4), and the resulting potassium binaphthyl phosphate salt is removed by filtration. The solvent composition preferably comprises, with respect to solvent (S4), about 10-15 mole % water and less than about 20 mole % solvent (S1). Preferably, solvent (S1) is methanol.

The oxalic acid used in step (ii-b)(a) may be anhydrous or hydrated, preferably the oxalic acid is oxalic acid dihydrate. The crystallization may occur spontaneously following addition of oxalic acid as in reactive crystallization or crystallization may comprise applying suitable crystallization techniques such as cooling, concentration, seeding, and/or addition of a suitable solvent.

Isolation of the solid in step (ii-b)(c) may be accomplished by any suitable means including decantation, centrifugation, or filtration, preferably filtration.

The solid that is isolated in step (ii-b)(c) is isomerically enriched in the zuclomiphene oxalate salt in relation to the enclomiphene oxalate salt. Preferably, the isomeric ratio of zuclomiphene:enclomiphene in this isolated solid is in the range of about 90:10 to about 100:0, more preferably it is in the range of about 95:5 to about 100:0, even more preferably, it is in the range of about 97:3 to about 100:0. Most preferably, the solid that is isolated is substantially isomerically pure zuclomiphene oxalate salt.

Preferably, the solid that is isolated from the suspension is a new crystalline salt of zuclomiphene, crystalline zuclomiphene oxalate, and is most preferably crystalline zuclomiphene oxalate Form APO-I as described herein.

In a second embodiment of the present invention, there is provided a process for the preparation of a solid that is isomerically enriched in zuclomiphene of Formula (1-A) relative to enclomiphene of Formula (1-B):

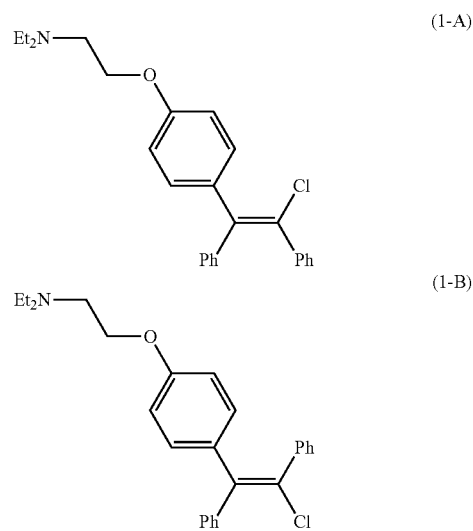

or a salt thereof, the process comprising:
(i) providing a first solution of zuclomiphene binaphthyl hydrogen phosphate salt in a solvent (S5), wherein the salt has an initial isomeric purity of at least about 75% (Z);

and either:
(ii-a) crystallizing and isolating a solid from the first solution that is isomerically enriched in the zuclomiphene binaphthyl hydrogen phosphate salt; or
(ii-b)(a) treating the first solution with a base to liberate binaphthyl phosphate salt and removing it from the first solution to afford a second solution;
(b) treating the second solution with oxalic acid; and
(c) crystallizing and isolating a solid from the second solution that is isomerically enriched in the zuclomiphene oxalate salt;

The solution of zuclomiphene binaphthyl hydrogen phosphate salt in step (i) may be the mother liquor derived from a prior fractional crystallization process applied to a composition comprising clomiphene isomers, or salts thereof, as described herein. Alternatively, the solution may be derived from any other means including dissolving zuclomiphene binaphthyl hydrogen phosphate salt having the requisite isomeric purity in the solvent (S5) or by treating zuclomiphene free base or an alternate salt thereof having the requisite isomeric purity with binaphthyl hydrogen phosphate in a solvent (S5).

The solvent (S5) may be selected from the group consisting of C1-C3 alcohols and mixtures thereof with an alkyl ether. Preferably, the solvent (S5) is methanol or a mixture of methanol and methyl t-butyl ether.

In the embodiment proceeding through step (ii-a), crystallizing a solid may comprise any one or more of the following steps: stirring and maintaining the solution for a suitable time; cooling the solution; adding a solvent (S6) to the solution; increasing the concentration of the solution; and seeding the solution. Preferably, the solution is stirred for a suitable time to encourage crystallization, preferably for a suitable time in the range of about 2 hours to about 20 hours, most preferably the suitable time is in the range of about 4 hours to about 8 hours. Preferably, the solution is concentrated to a lower volume than the initial volume of the solution, preferably it is concentrated to a volume, in relation to the combined mass of enclomiphene binaphthyl hydrogen phosphate salt and zuclomiphene binaphthyl hydrogen phosphate salt (which can be calculated as described above) in the range of about 3 volumes to about 5 volumes. Preferably, the solution is treated with a solvent (S6) to lower the solubility of the salt that is preferably an alkyl ether. More preferably, the solvent (S6) is selected from the group consisting of methyl t-butyl ether, tetrahydrofuran, and 2-methyltetrahydrofuran. Most preferably, the solvent (S6) is methyl t-butyl ether. Preferably, the solution is cooled to a temperature in the range of about 0° C. to about 10° C., most preferably the temperature is in the range of about 0° C. to about 5° C.

Isolation of the solid in step (ii-a) may be accomplished by any suitable means including decantation, centrifugation, or filtration, preferably filtration.

The solid that is isolated in step (ii-a) is isomerically enriched in the zuclomiphene binaphthyl hydrogen phosphate salt in relation to the enclomiphene binaphthyl hydrogen phosphate salt. Preferably, the isomeric ratio of zuclomiphene:enclomiphene in the isolated solid is in the range of about 90:10 to about 100:0, more preferably it is in the range of about 95:5 to about 100:0, even more preferably, it is in the range of about 97:3 to about 100:0. Most preferably, the solid that is isolated is substantially isomerically pure zuclomiphene binaphthyl hydrogen phosphate salt.

Preferably, the solid that is isolated in step (ii-a) is a new crystalline salt of zuclomiphene, crystalline zuclomiphene binaphthyl hydrogen phosphate, and is most preferably crystalline zuclomiphene binaphthyl hydrogen phosphate Form APO-I as described herein.

The solid that is isolated from the suspension may be further converted to an alternative zuclomiphene salt thereof or to zuclomiphene free base as described in the first embodiment herein. Preferably, the solid is further converted to zuclomiphene oxalate salt by the process described in the first embodiment herein.

In the embodiment proceeding through steps (ii-b)(a), (ii-b)(b), and (ii-b)(c), the first solution is treated with base to liberate the free base forms of enclomiphene and zuclomiphene from the binaphthyl hydrogen phosphate. Preferably, a portion of the solvent (S5) comprising the first solution is replaced with solvent (S7) that is selected from the group consisting of esters, ethers, and ketones. Preferably, the solvent (S7) is selected from the group consisting of ethyl acetate, methyl ethyl ketone, acetone, and mixtures thereof. Most preferably, the solvent (S7) is ethyl acetate or a mixture thereof with acetone. Preferably, the suitable volume of solvent (S7) in relation to the combined mass of enclomiphene binaphthyl hydrogen phosphate salt and zuclomiphene binaphthyl hydrogen phosphate salt (which can be calculated as described above) is in the range of about 3 volumes to about 8 volumes, more preferably in the range of about 3 volumes to about 5 volumes.

In a preferred embodiment of step (ii-b)(a), the binaphthyl hydrogen phosphate is removed from the first solution by filtration of an insoluble binaphthyl phosphate salt formed by treatment of the first solution with the base. The base may be selected from the group consisting of potassium carbonate, sodium carbonate, potassium hydroxide, and sodium hydroxide. Preferably, the base is potassium carbonate which is added as a solid, along with a minimum amount of water, to the first solution comprising solvent (S7), and the resulting potassium binaphthyl phosphate salt is removed by filtration. The solvent composition preferably comprises, with respect to solvent (S7), about 10-15 mole % water and less than about 20 mole % solvent (S5). Preferably, solvent (S5) is methanol.

The oxalic acid used in step (ii-b)(a) may be anhydrous or hydrated, preferably the oxalic acid is oxalic acid dihydrate. The crystallization may occur spontaneously following addition of oxalic acid as in reactive crystallization or crystallization may comprise applying suitable crystallization techniques such as cooling, concentration, seeding, and/or addition of a suitable solvent.

Isolation of the solid in step (ii-b)(c) may be accomplished by any suitable means including decantation, centrifugation, or filtration, preferably filtration.

The solid that is isolated in step (ii-b)(c) is isomerically enriched in the zuclomiphene oxalate salt in relation to the enclomiphene oxalate salt. Preferably, the isomeric ratio of zuclomiphene:enclomiphene in this isolated solid is in the range of about 90:10 to about 100:0, more preferably it is in the range of about 95:5 to about 100:0, even more preferably, it is in the range of about 97:3 to about 100:0. Most preferably, the solid that is isolated is substantially isomerically pure zuclomiphene oxalate salt.

Preferably, the solid that is isolated from the suspension is a new crystalline salt of zuclomiphene, crystalline zuclomiphene oxalate, and is most preferably crystalline zuclomiphene oxalate Form APO-I as described herein.

The present invention provides direct and simple procedures for the isolation of zuclomiphene binaphthyl hydrogen phosphate salt and zuclomiphene oxalate salt, which are useful as intermediates in the preparation of zuclomiphene citrate, that are preferably substantially isomerically pure. As shown in Comparative Example 1, reproduction of conditions analogous to those of Example 32 of U.S. Pat. No. 3,848,030 A, provides zuclomiphene citrate having an isomeric ratio of zuclomiphene:enclomiphene of about 92:8, which necessitates further purification to afford isomerically pure material.

In another embodiment of the present invention, there is provided a new crystalline salt of zuclomiphene, zuclomiphene binaphthyl hydrogen phosphate salt.

In another embodiment of the present invention, there is provided a new crystalline form of zuclomiphene binaphthyl hydrogen phosphate salt, Form APO-I.

Zuclomiphene binaphthyl hydrogen phosphate Form APO-I can be characterized by a PXRD diffractogram comprising, among other peaks, characteristic peaks, expressed in degrees 2θ (±0.2°), at 9.2°, 10.5° and 12.0°. Preferably, the PXRD diffractogram further comprises at least three peaks, expressed in degrees 2θ (±0.2°), selected from the group consisting of 4.0°, 7.9°, 11.0°, 13.0°, 16.0°, 17.0° and 19.2°. More preferably, the PXRD diffractogram further comprises peaks, expressed in degrees 2θ (±0.2°), at 4.0°, 7.9°, 11.0°, 13.0°, 16.0°, 17.0° and 19.2°.

An illustrative PXRD diffractogram of zuclomiphene binaphthyl hydrogen phosphate Form APO-I, as prepared in Example 2, is shown in FIG. 1. A peak listing, comprising representative peaks from the PXRD diffractogram in FIG. 1, and their relative intensities, is provided in Table 1. Although illustrative of the PXRD diffractogram that is provided for the zuclomiphene binaphthyl hydrogen phosphate Form APO-I of the present invention, the relative intensities of the peaks are variable. Thus, depending on a particular sample, the prominence or relative intensity of the peaks observed may differ from those in the illustrative PXRD diffractogram and peak listing.

TABLE 1

Relative peak intensities of
zuclomiphene binaphthyl hydrogen phosphate
Form APO-I from FIG. 1

| Angle (2θ) | Relative intensity (%) |
|---|---|
| 4.0 | 3.5 |
| 7.9 | 2.4 |
| 9.2 | 5.7 |
| 10.5 | 39.1 |
| 11.0 | 16.9 |
| 12.0 | 71.8 |
| 13.0 | 10.1 |
| 14.5 | 5.4 |
| 16.0 | 22.9 |
| 17.0 | 13.5 |
| 18.1 | 10.1 |
| 19.2 | 100.0 |
| 20.9 | 6.9 |
| 21.9 | 8.0 |
| 22.5 | 12.3 |
| 24.5 | 9.5 |

Figure 2:
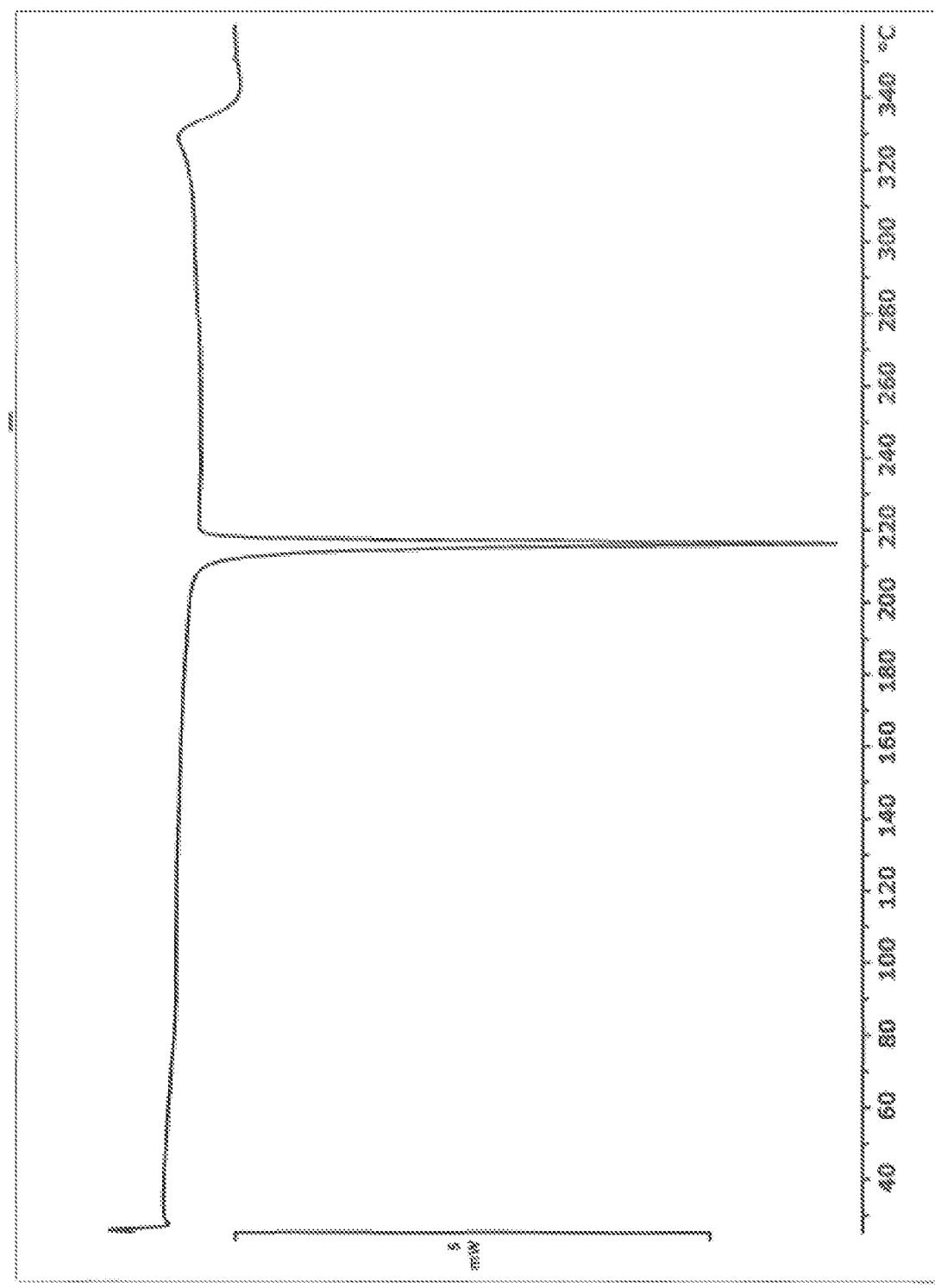
FIG. 2 is a representative DSC thermogram of zuclomiphene binaphthyl hydrogen phosphate Form APO-I as prepared in Example 2.

An illustrative DSC thermogram of zuclomiphene binaphthyl hydrogen phosphate Form APO-I is shown in FIG. 2. The DSC thermogram may be further characterized by an endothermic peak with a peak onset at about 214° C. and a peak maximum at about 216° C.

In another embodiment of the present invention, there is provided a new crystalline salt of zuclomiphene, zuclomiphene oxalate salt.

In another embodiment of the present invention, there is provided a new crystalline form of zuclomiphene oxalate salt, Form APO-I.

Zuclomiphene oxalate Form APO-I can be characterized by a PXRD diffractogram comprising, among other peaks, characteristic peaks, expressed in degrees 2θ (±0.2°), at 6.5°, 13.1° and 14.5°. Preferably, the PXRD diffractogram further comprises at least three peaks, expressed in degrees 2θ (±0.2°), selected from the group consisting of 11.1°, 12.5°, 16.4°, 17.7°, 18.8°, 19.6°, 20.5°, 21.4°, 22.4° and 25.2°. More preferably, the PXRD diffractogram further comprises peaks, expressed in degrees 2θ (±0.2°), at 11.1°, 12.5°, 16.4°, 17.7°, 18.8°, 19.6°, 20.5°, 21.4°, 22.4° and 25.2°.

Figure 3:
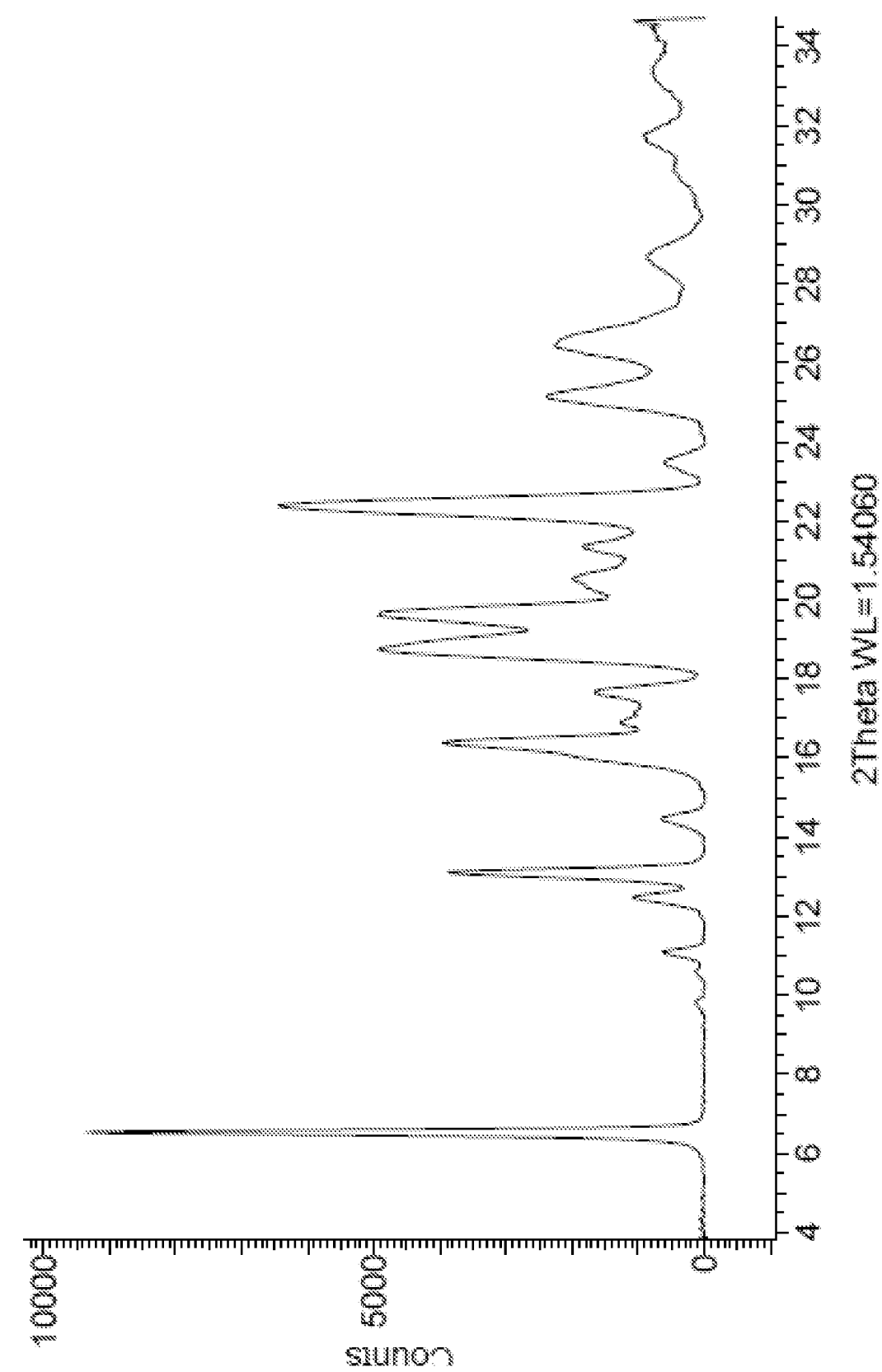
FIG. 3 is a representative PXRD diffractogram of zuclomiphene oxalate salt Form APO-I as prepared in Example 6.

An illustrative PXRD diffractogram of zuclomiphene oxalate Form APO-I, as prepared in Example 6, is shown in FIG. 3. A peak listing, comprising representative peaks from the PXRD diffractogram in FIG. 3, and their relative intensities, is provided in Table 2. Although illustrative of the PXRD diffractogram that is provided for the zuclomiphene oxalate Form APO-I of the present invention, the relative intensities of the peaks are variable. Thus, depending on a particular sample, the prominence or relative intensity of the peaks observed may differ from those in the illustrative PXRD diffractogram and peak listing.

TABLE 2

Relative peak intensities of
zuclomiphene oxalate Form APO-I from FIG. 3

| Angle (2θ) | Relative intensity (%) |
|---|---|
| 6.53 | 100.0 |
| 11.10 | 6.8 |
| 12.48 | 11.6 |
| 13.11 | 41.4 |
| 14.46 | 6.9 |
| 16.39 | 42.4 |
| 17.67 | 17.7 |

TABLE 2-continued

Relative peak intensities of
zuclomiphene oxalate Form APO-I from FIG. 3

| Angle (2θ) | Relative intensity (%) |
|---|---|
| 18.75 | 52.9 |
| 19.62 | 52.9 |
| 20.53 | 21.4 |
| 21.36 | 19.8 |
| 22.38 | 69.1 |
| 25.16 | 25.8 |
| 26.45 | 24.3 |

Figure 4:
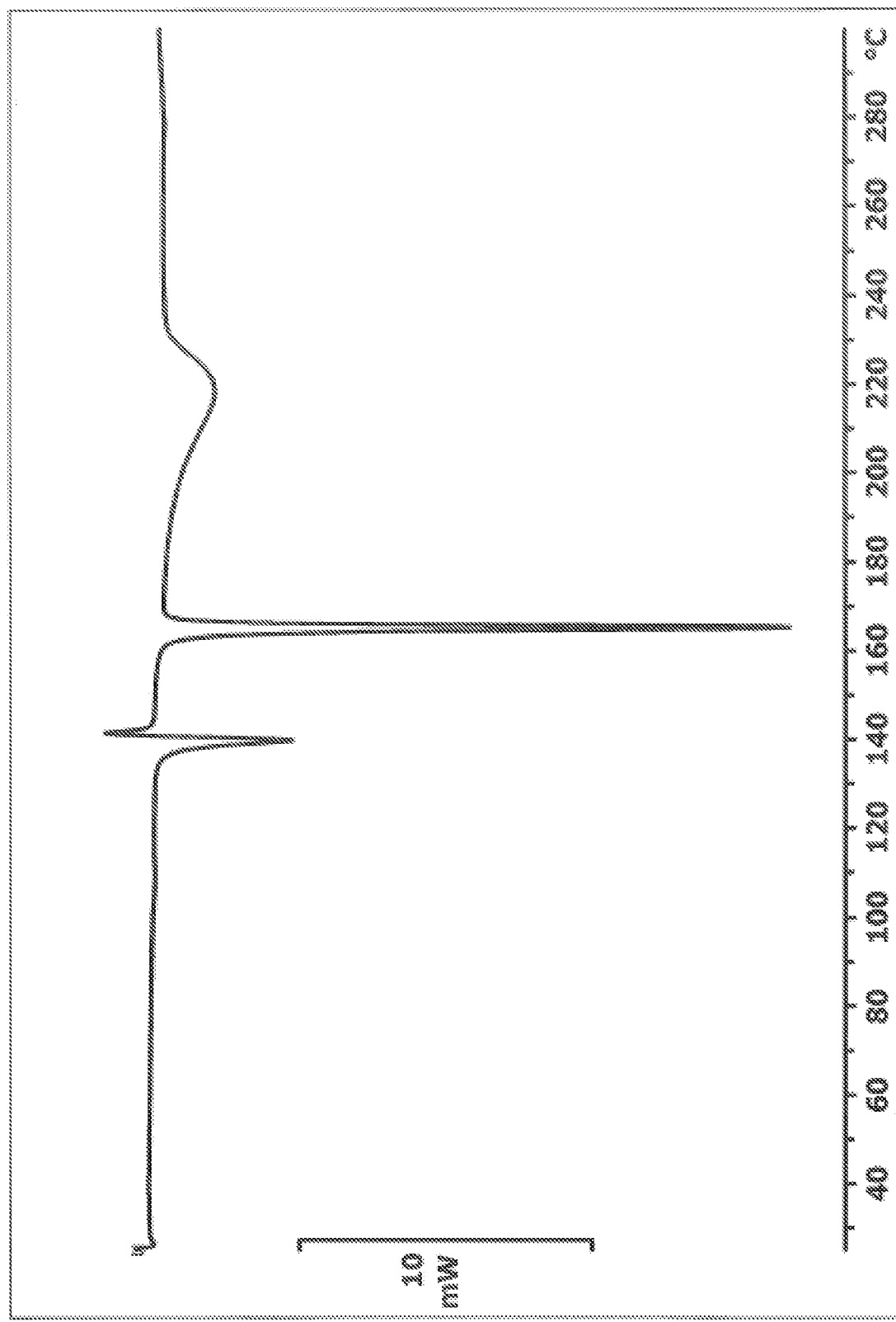
FIG. 4 is a representative DSC thermogram of zuclomiphene oxalate salt Form APO-I as prepared in Example 6.

An illustrative DSC thermogram of zuclomiphene oxalate Form APO-I is shown in FIG. 4. The DSC thermogram may be further characterized by a first endothermic peak with a peak onset at about 137° C. and a peak maximum at about 139° C., an exothermic peak with an onset at about 141° C., and a second endothermic peak with a peak onset at about 163° C. and a peak maximum at about 164° C.

In another embodiment of the present invention, there is provided a new crystalline form of zuclomiphene oxalate salt, Form APO-II.

Zuclomiphene oxalate Form APO-II can be characterized by a PXRD diffractogram comprising, among other peaks, characteristic peaks, expressed in degrees 2θ (±0.2°), at 5.3°, 10.6° and 14.0°. Preferably, the PXRD diffractogram further comprises at least three peaks, expressed in degrees 2θ (±0.2°), selected from the group consisting of 10.2°, 12.0°, 13.4°, 14.7°, 15.9°, 16.3°, 18.6°, 20.0°, 20.6° and 22.7°. More preferably, the PXRD diffractogram further comprises peaks, expressed in degrees 2θ (±0.2°), at 10.2°, 12.0°, 13.4°, 14.7°, 15.9°, 16.3°, 18.6°, 20.0°, 20.6° and 22.7°.

Figure 5:
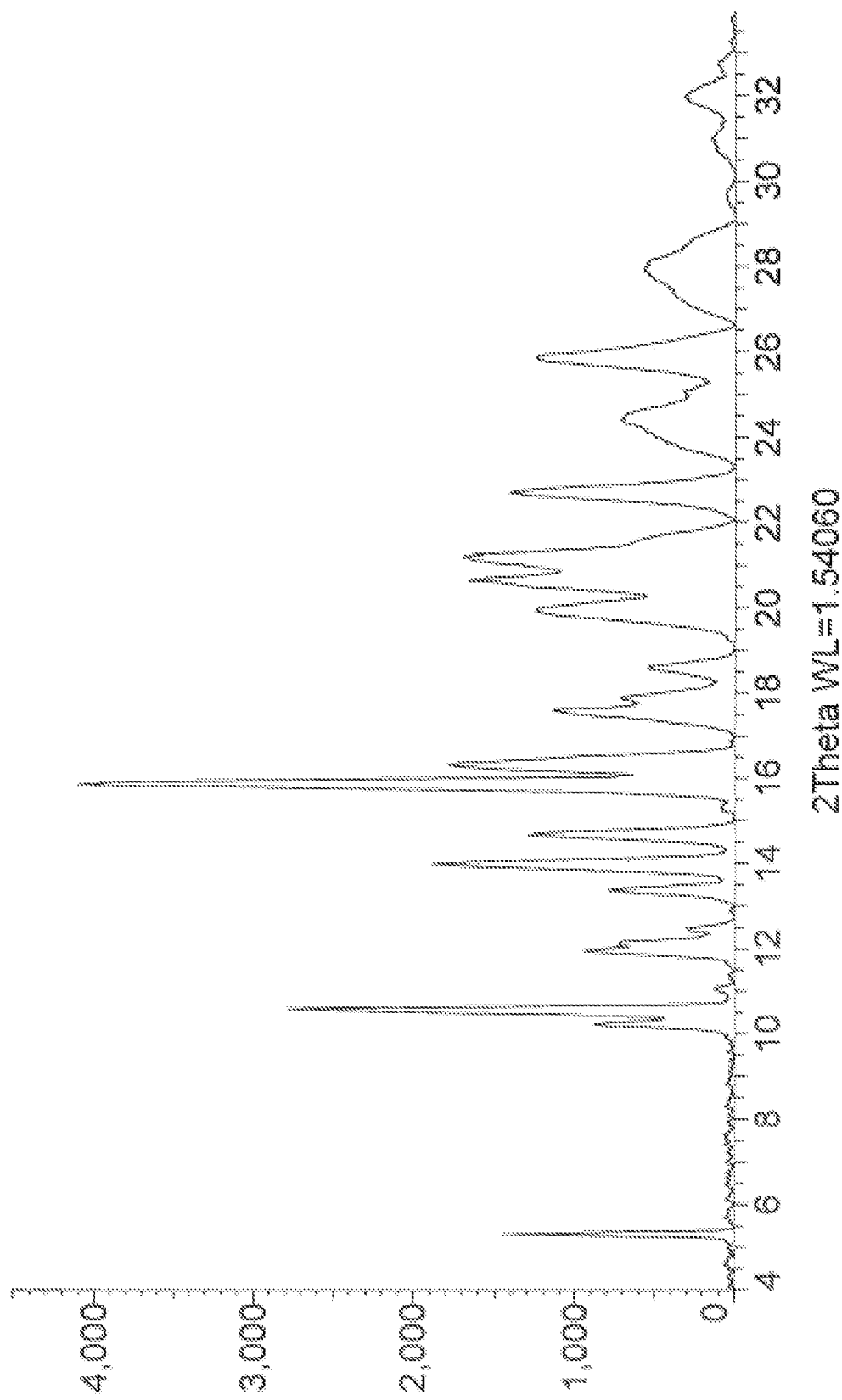
FIG. 5 is a representative PXRD diffractogram of zuclomiphene oxalate salt Form APO-II as prepared in Example 7.

An illustrative PXRD diffractogram of zuclomiphene oxalate Form APO-II, as prepared in Example 7, is shown in FIG. 5. A peak listing, comprising representative peaks from the PXRD diffractogram in FIG. 5, and their relative intensities, is provided in Table 3. Although illustrative of the PXRD diffractogram that is provided for the zuclomiphene oxalate Form APO-II of the present invention, the relative intensities of the peaks are variable. Thus, depending on a particular sample, the prominence or relative intensity of the peaks observed may differ from those in the illustrative PXRD diffractogram and peak listing.

TABLE 3

Relative peak intensities of
zuclomiphene oxalate Form APO-II from FIG. 5

| Angle (2θ) | Relative intensity (%) |
|---|---|
| 5.30 | 30.8 |
| 10.23 | 20.3 |
| 10.58 | 65.4 |
| 11.96 | 22.0 |
| 13.37 | 18.3 |
| 13.98 | 44.2 |
| 14.68 | 29.8 |
| 15.85 | 100.0 |
| 16.31 | 41.4 |
| 17.59 | 25.9 |
| 18.61 | 12.3 |
| 19.95 | 28.8 |
| 20.64 | 39.7 |
| 21.19 | 39.3 |
| 22.71 | 32.6 |
| 25.85 | 28.5 |

Figure 6:
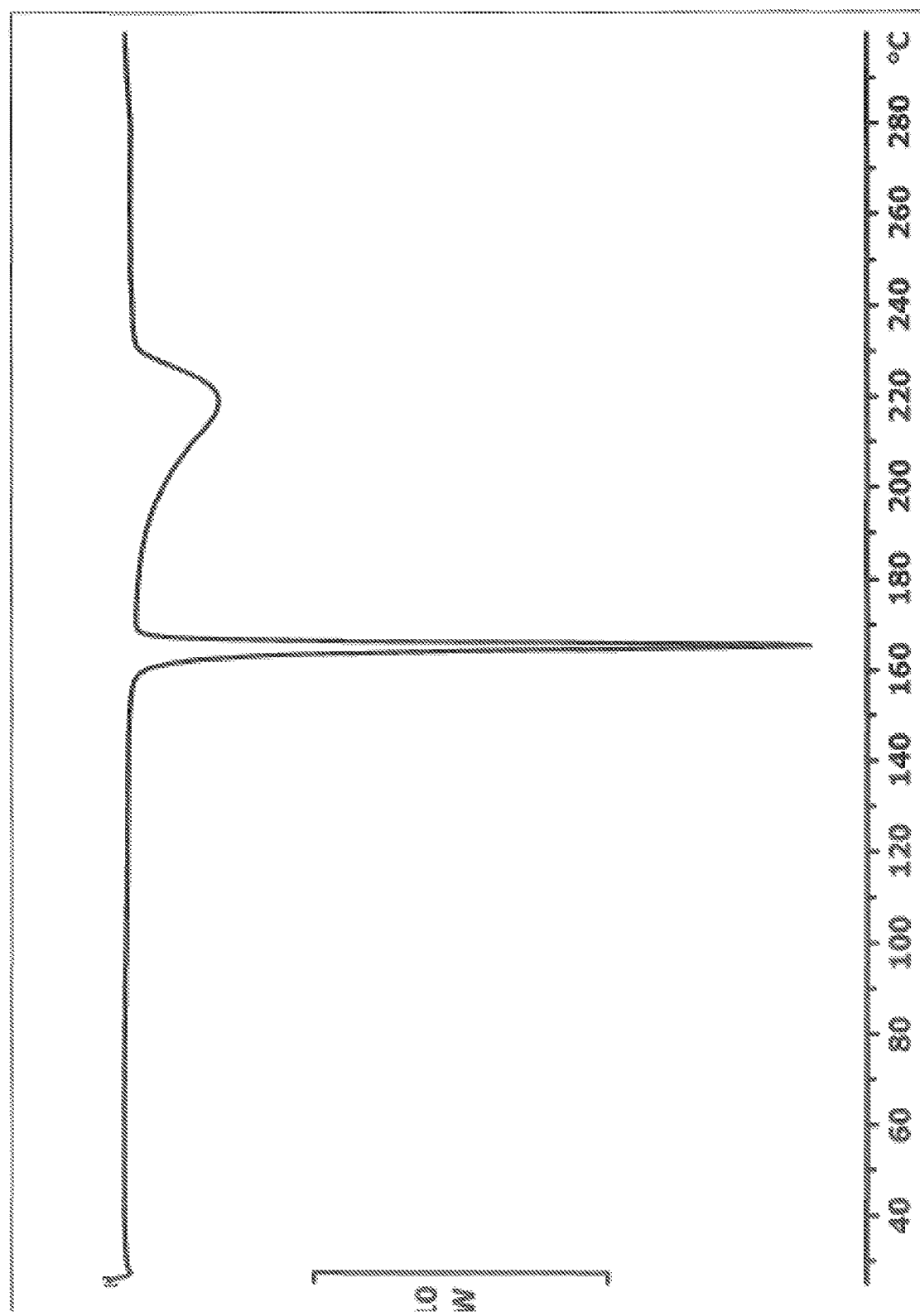
FIG. 6 is a representative DSC thermogram of zuclomiphene oxalate salt Form APO-II as prepared in Example 7.

An illustrative DSC thermogram of zuclomiphene oxalate Form APO-II is shown in FIG. 6. The DSC thermogram may be further characterized by an endothermic peak with a peak onset at about 163° C. and a peak maximum at about 164° C.

In another embodiment of the present invention, there is provided a new crystalline form of zuclomiphene oxalate salt, Form APO-III.

Zuclomiphene oxalate Form APO-III can be characterized by a PXRD diffractogram comprising, among other peaks, characteristic peaks, expressed in degrees 2θ (±0.2°), at 5.2°, 17.0° and 18.9°. Preferably, the PXRD diffractogram further comprises at least three peaks, expressed in degrees 2θ (±0.2°), selected from the group consisting of 9.8°, 10.2°, 10.5°, 12.3°, 14.1°, 17.7°, 19.7°, 20.7°, 23.0° and 25.6°. More preferably, the PXRD diffractogram further comprises peaks, expressed in degrees 2θ (±0.2°), at 9.8°, 10.2°, 10.5°, 12.3°, 14.1°, 17.7°, 19.7°, 20.7°, 23.0° and 25.6°.

Figure 7:
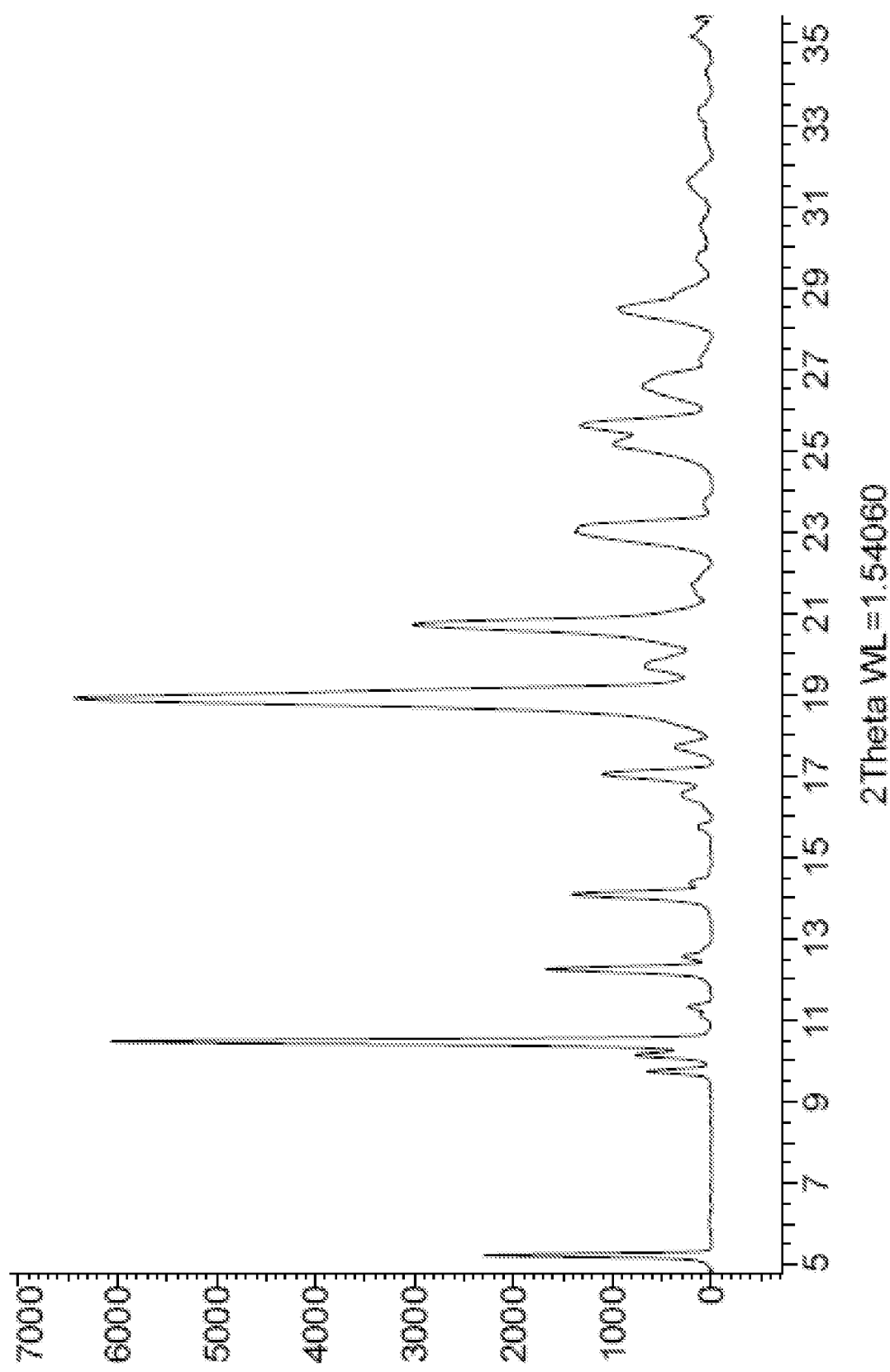
FIG. 7 is a representative PXRD diffractogram of zuclomiphene oxalate salt Form APO-III as prepared in Example 8.

An illustrative PXRD diffractogram of zuclomiphene oxalate Form APO-III, as prepared in Example 8, is shown in FIG. 7. A peak listing, comprising representative peaks from the PXRD diffractogram in FIG. 7, and their relative intensities, is provided in Table 4. Although illustrative of the PXRD diffractogram that is provided for the zuclomiphene oxalate Form APO-III of the present invention, the relative intensities of the peaks are variable. Thus, depending on a particular sample, the prominence or relative intensity of the peaks observed may differ from those in the illustrative PXRD diffractogram and peak listing.

TABLE 4

Relative peak intensities of zuclomiphene oxalate Form APO-III from FIG. 7

| Angle (2θ) | Relative intensity (%) |
| --- | --- |
| 5.22 | 35.4 |
| 9.75 | 10.0 |
| 10.15 | 11.9 |
| 10.48 | 93.5 |
| 12.26 | 25.7 |
| 14.10 | 21.8 |
| 17.05 | 17.1 |
| 17.71 | 5.7 |
| 18.91 | 100.0 |
| 19.68 | 10.5 |
| 20.72 | 46.9 |
| 23.04 | 21.0 |
| 25.61 | 20.5 |

Figure 8:
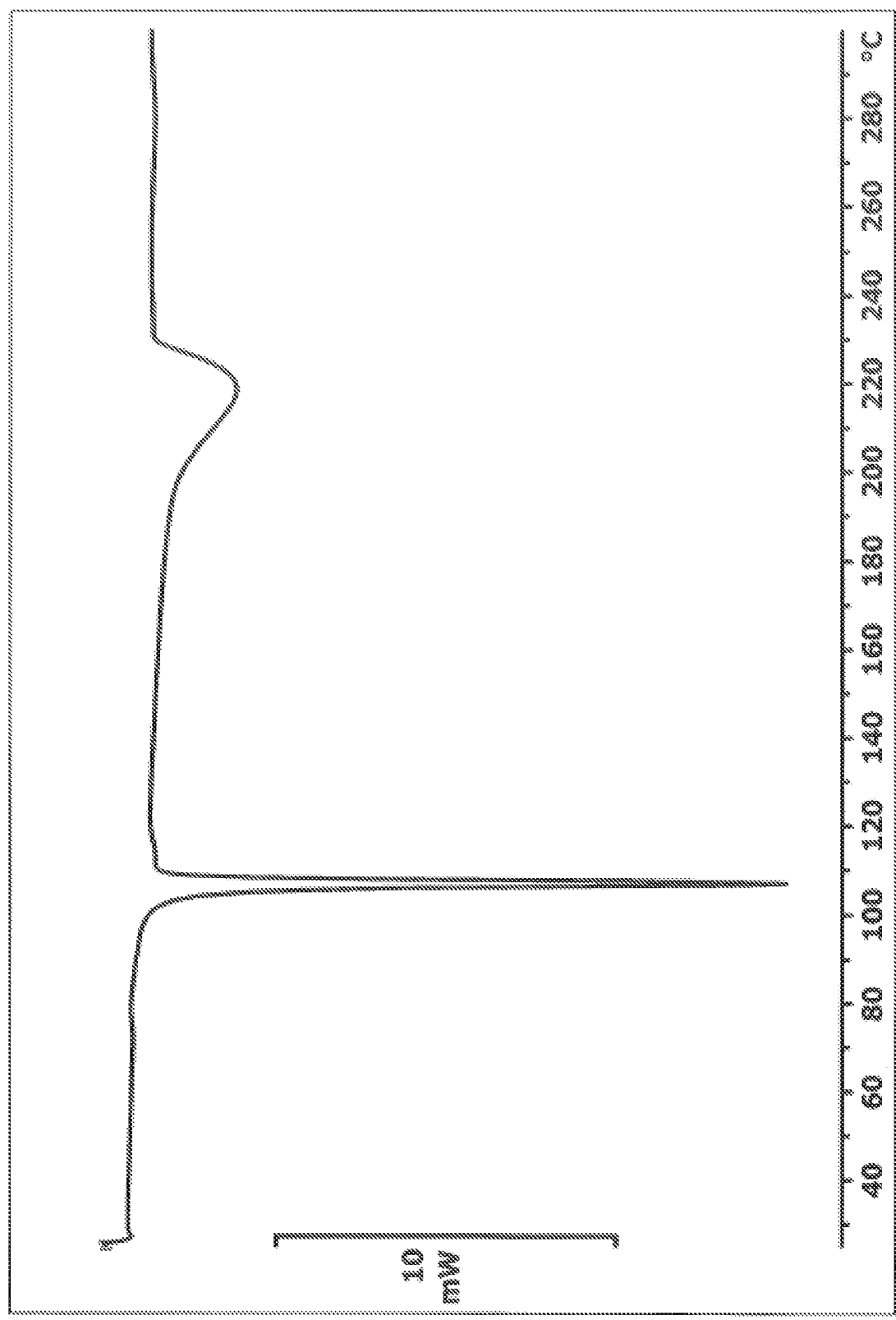
FIG. 8 is a representative DSC thermogram of zuclomiphene oxalate salt Form APO-III as prepared in Example 8.

An illustrative DSC thermogram of zuclomiphene oxalate Form APO-III is shown in FIG. 8. The DSC thermogram may be further characterized by an endothermic peak with a peak onset at about 105° C. and a peak maximum at about 106° C.

In another embodiment of the present invention, there is provided a new crystalline form of zuclomiphene oxalate salt, Form APO-IV.

Zuclomiphene oxalate Form APO-IV can be characterized by a PXRD diffractogram comprising, among other peaks, characteristic peaks, expressed in degrees 2θ (±0.2°), at 6.8°, 10.2° and 18.5°. Preferably, the PXRD diffractogram further comprises at least three peaks, expressed in degrees 2θ (±0.2°), selected from the group consisting of 12.8°, 13.7°, 15.1°, 16.0°, 16.8°, 19.4°, 20.3°, 22.6°, 23.3° and 24.7°. More preferably, the PXRD diffractogram further comprises peaks, expressed in degrees 2θ (±0.2°), at 12.8°, 13.7°, 15.1°, 16.0°, 16.8°, 19.4°, 20.3°, 22.6°, 23.3° and 24.7°.

Figure 9:
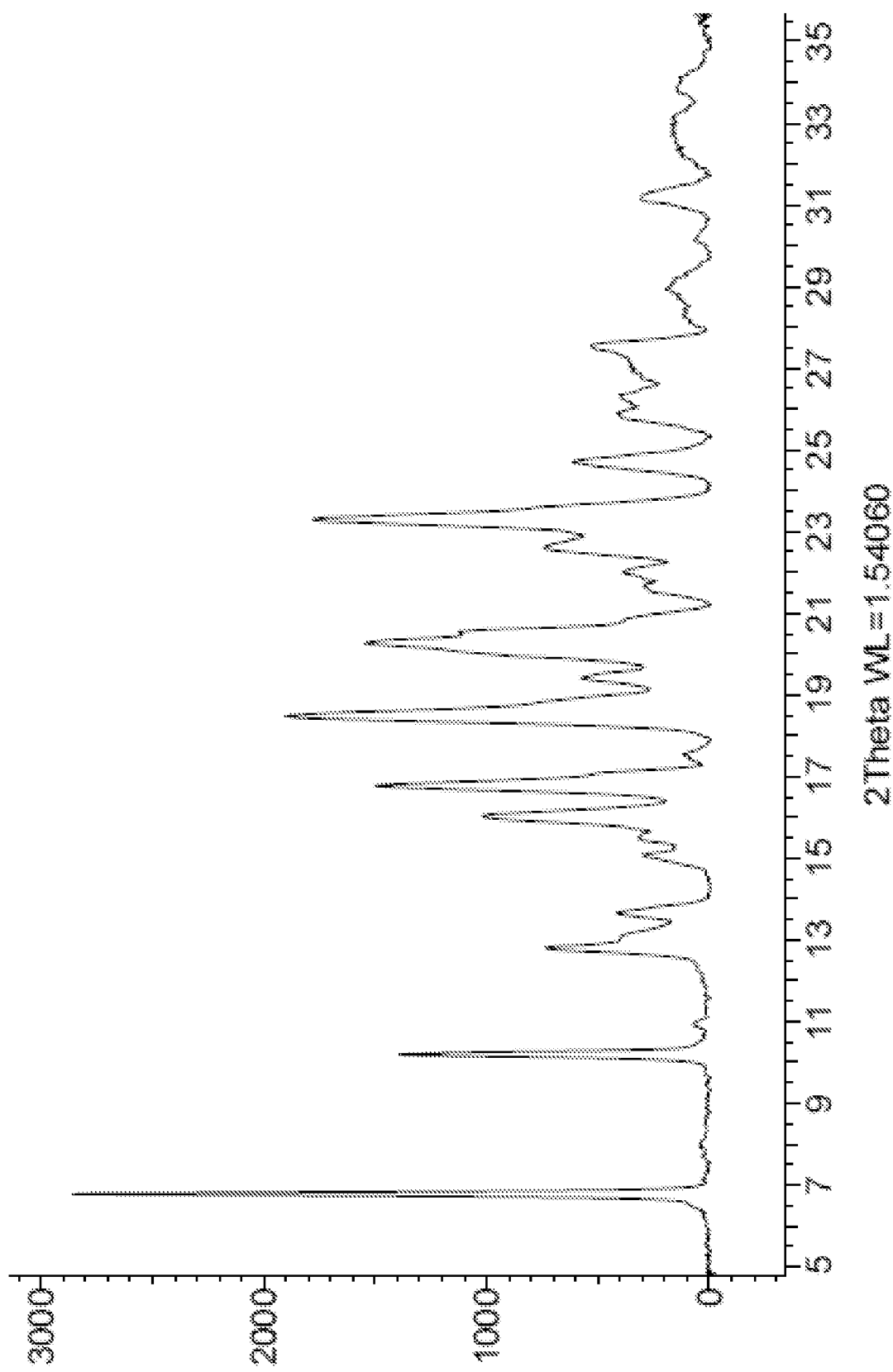
FIG. 9 is a representative PXRD diffractogram of zuclomiphene oxalate salt Form APO-IV as prepared in Example 9.

An illustrative PXRD diffractogram of zuclomiphene oxalate Form APO-IV, as prepared in Example 9, is shown in FIG. 9. A peak listing, comprising representative peaks from the PXRD diffractogram in FIG. 9, and their relative intensities, is provided in Table 5. Although illustrative of the PXRD diffractogram that is provided for the zuclomiphene oxalate Form APO-IV of the present invention, the relative intensities of the peaks are variable. Thus, depending on a particular sample, the prominence or relative intensity of the peaks observed may differ from those in the illustrative PXRD diffractogram and peak listing.

TABLE 5

Relative peak intensities of zuclomiphene oxalate Form APO-IV from FIG. 9

| Angle (2θ) | Relative intensity (%) |
| --- | --- |
| 6.79 | 100.0 |
| 10.20 | 48.8 |
| 12.80 | 26.0 |
| 13.65 | 14.7 |
| 15.08 | 10.5 |
| 16.03 | 35.8 |
| 16.78 | 52.9 |
| 18.48 | 67.1 |
| 19.42 | 20.3 |
| 20.27 | 54.5 |
| 22.61 | 26.3 |
| 23.29 | 62.8 |
| 24.71 | 21.6 |

Figure 10:
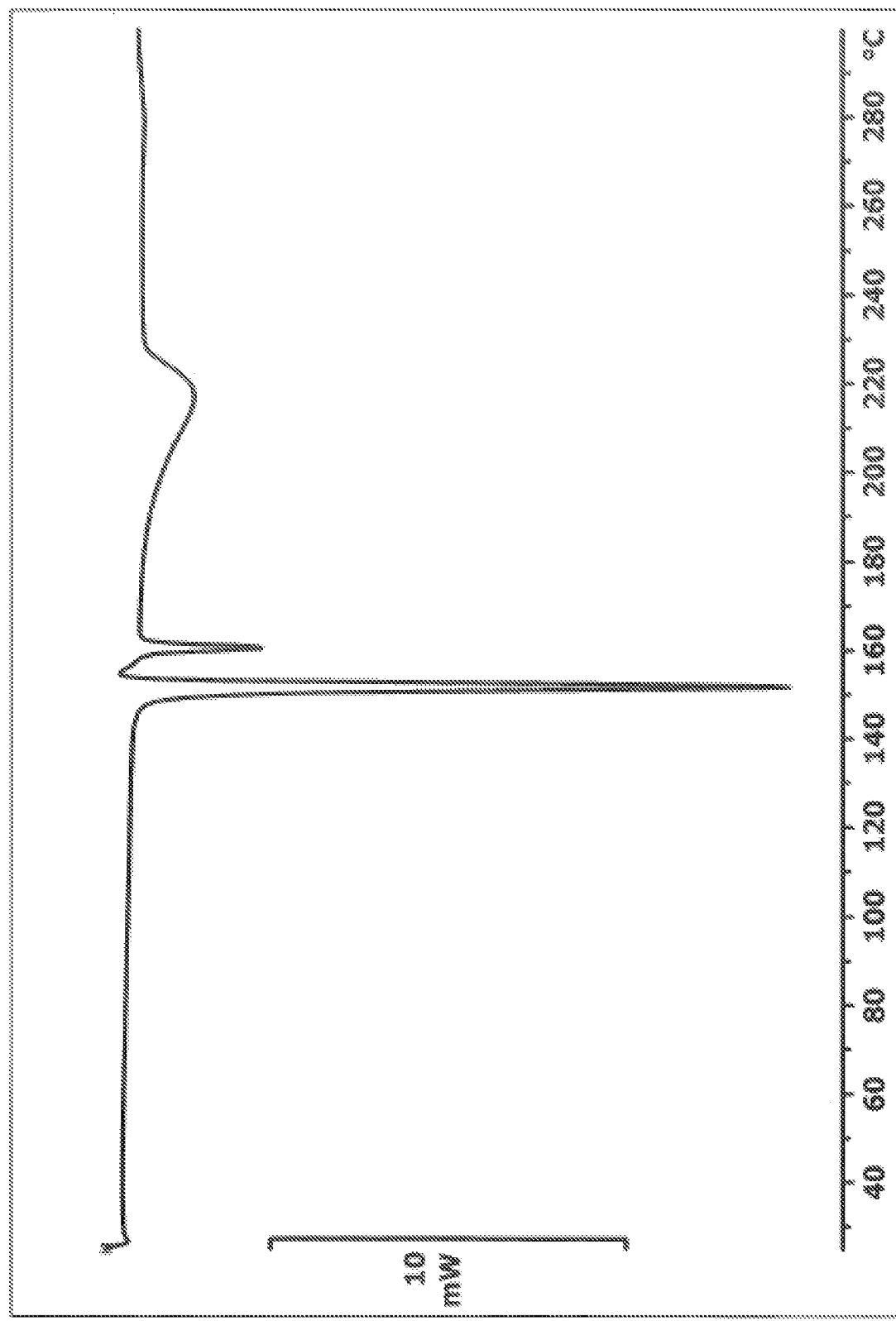
FIG. 10 is a representative DSC thermogram of zuclomiphene oxalate salt Form APO-IV as prepared in Example 9.

An illustrative DSC thermogram of zuclomiphene oxalate Form APO-IV is shown in FIG. 10. The DSC thermogram may be further characterized by an endothermic peak with a peak onset at about 150° C. and a peak maximum at about 151° C.

EXAMPLES

The following non-limiting examples are illustrative of some of the aspects and embodiments of the invention described herein.

The clomiphene citrate salt used in the following examples was commercially available.

PXRD Analysis:

Data was acquired on a PANanalytical X-Pert Pro MPD diffractometer with fixed divergence slits and an X'Celerator RTMS detector. The diffractometer was configured in Bragg-Brentano geometry; data was collected over a 2-theta range of 3° to 40° using CuKα radiation at a power of 40 mA and 45 kV. CuKβ radiation was removed using a divergent beam nickel filter. A step size of 0.017° was used. The sample was rotated to reduce preferred orientation effects. The sample was lightly ground prior to analysis.

Differential Scanning calorimetry Analysis:

DSC thermograms were collected on a Mettler-Toledo 821e instrument. Samples (2±0.2 mg) were weighed into separate 40 μL aluminum pans, and were crimped closed with aluminum lids having a 50 μm perforation. The samples were analyzed under a flow of nitrogen (50±5 mL/min) at a scan rate of 10° C./minute between 25° C. and 300° C.

Temperature Cycling Program:

Temperature cycling in Examples 8 and 9 was conducted as follows: 50° C., 2 h; 40° C., 1 h; 30° C., 1 h; 20° C., 1 h; 10° C., 1 h; 5° C., 1 h; 40° C., 1 h; 30° C., 1 h; 20° C., 1 h; 10° C., 1 h; 5° C., 1 h; 30° C., 1 h; 20° C., 1 h; 10° C., 1 h; 5° C., 1 h.

Comparative Example 1: Preparation of Zuclomiphene Citrate Using Conditions Analogous to U.S. Pat. No. 3,848,030 A Methanol (35 mL) was added to a mixture of clomiphene citrate ((1)·(citric acid), E:Z isomeric ratio 60:40, 10 g, 0.0167 mol) and racemic binaphthyl hydrogen phosphate (5.82 g, 0.0167). Initially, a clear brown solution was obtained, which became turbid after about 10 minutes and then formed a thick paste which stuck to the flask walls; heating the thick paste to 45-50° C. for about one hour did not affect the consistency. Methanol (20 mL) was charged and heating was continued for an additional hour, but the reaction mixture remained as a creamy paste. Heating was discontinued and the mixture was stirred for two hours, however the consistency of the material remained unchanged. The unpourable material was scooped out of the flask and the flask was washed with methanol (4×10 mL) to facilitate effective transfer. The damp cake was dried in vacuo at 50-60° C. for about 18 hours to afford solid enclomiphene binaphthyl hydrogen phosphate ((1-B)·(BPA), 7.30 g, 96.5% recovery of available) as a white to off-white solid. The solid was determined to have an isomeric purity of about 94.6% (E) by $^1$H NMR.

The resulting mother liquor was concentrated to about 3 volumes (30 mL), water (50 mL) was charged and the pH of the mixture was adjusted to 9-10. Methyl t-butyl ether (140 mL) was charged to the gummy mass and the phases were separated. The aqueous layer was extracted with methyl t-butyl ether (2×140 mL) and the combined organic layer was washed with water (50 mL). A solution of citric acid (1.35 g) in ethanol (3.3 mL) was added to the organic layer and the mixture was stirred at room temperature for about 5 hours. The resulting solid was collected by filtration and dried in vacuo at 45-50° C. to afford zuclomiphene citrate ((1-A)·(citric acid), 3.5 g, 87.5% recovery of available). The solid was determined to have an isomeric purity of about 92.2% (Z) by $^1$H NMR.

Example 1: Preparation of Solid Zuclomiphene Binaphthyl Hydrogen Phosphate Salt (1-A)·(BPA)

To a solution of clomiphene citrate ((1)·(citric acid), E:Z isomeric ratio 60:40, 20 g, 0.0334 mol) in methanol (240 mL) was added racemic binaphthyl hydrogen phosphate (BPA) (12.2 g, 0.0351) in six portions over two hours at room temperature. Methyl t-butyl ether (60 mL) was added to the suspension and stirring was maintained for about five hours to afford a uniform mixture. The mixture was filtered at room temperature, the cake was washed with 20% methyl t-butyl ether in methanol (2×20 mL), and the solid was dried in vacuo at 40-45° C. for about 64 hours to afford solid enclomiphene binaphthyl hydrogen phosphate ((1-B)·(BPA), 13.6 g, 89.9% recovery of available). The solid did not contain detectable levels of zuclomiphene binaphthyl hydrogen phosphate by $^1$H NMR.

The resulting mother liquor was stirred at room temperature for about 64 hours. During this time, a suspension formed, which was cooled to 0-5° C. and stirred for about seven hours. The solid was isolated by filtration followed by drying in vacuo at 45-50° C. to afford solid zuclomiphene binaphthyl hydrogen phosphate ((1-A)·(BPA), 5.8 g, 57.5% recovery of available). The solid did not contain detectable levels of enclomiphene binaphthyl hydrogen phosphate by $^1$H NMR.

$^1$H NMR of enclomiphene binaphthyl hydrogen phosphate (1-B)·(BPA) (DMSO-$d_6$, 300 MHz) δ: 1.10 (t, J=7.2 Hz, 6H), 3.20-2.90 (m, 4H), 3.50-3.25 (m, 2H+H$_2$O), 4.14 (t, J=4.7 Hz, 2H), 6.70 (d, J=8.8 Hz, 2H), 6.86 (d, J=8.7 Hz, 2H), 7.50-7.10 (m, 18H), 8.02 (d, J=3.5 Hz, 4H), 10.08 (bs, 1H).

$^1$H NMR of zuclomiphene binaphthyl hydrogen phosphate (1-A)·(BPA) (DMSO-$d_6$, 300 MHz) δ: 1.17 (t, J=7.2 Hz, 6H), 3.25-3.00 (m, 4H), 3.55-3.40 (m, 2H), 4.30 (t, J=4.8 Hz, 2H), 7.05-6.90 (m, 4H), 7.20-7.10 (m, 3H), 7.45-7.12 (m, 11H), 7.50-7.35 (m, 4H), 8.10-7.90 (m, 4H), 9.90 (bs, 1H).

Example 2: Preparation of Solid Zuclomiphene Binaphthyl Hydrogen Phosphate Salt (1-A)·(BPA) Form APO-1

To a suspension of racemic binaphthyl hydrogen phosphate (BPA) (12.2 g, 0.0351) in methanol (80 mL) and methyl t-butyl ether (80 mL) was added a solution of clomiphene citrate ((1)·(citric acid), E:Z isomeric ratio 60:40, 20 g, 0.0334 mol) in methanol (200 mL) via addition funnel over two hours at room temperature. The resulting suspension was stirred at room temperature for about 4 hours to afford a uniform slurry. The mixture was filtered at room temperature, the cake was washed with methanol (2×20 mL) and dried in vacuo at 40-45° C. for about 16 hours to afford solid enclomiphene binaphthyl hydrogen phosphate ((1-B)·(BPA), 13.6 g, 89.9% recovery of available). The solid did not contain detectable levels of zuclomiphene binaphthyl hydrogen phosphate by $^1$H NMR.

The resulting mother liquor was maintained at room temperature for about 18 hours. During this time, a suspension formed, which was cooled to 0-5° C. and stirred for about six hours. The solid was collected by filtration followed by drying in vacuo at 45-50° C. to afford solid zuclomiphene binaphthyl hydrogen phosphate Form APO-1 ((1-A)·(BPA), 4.9 g, 48.6% recovery of available). The solid did not contain detectable levels of enclomiphene binaphthyl hydrogen phosphate by $^1$H NMR. The PXRD diffractogram and DSC thermogram of a sample prepared by this method are provided in FIG. 1 and FIG. 2, respectively.

Example 3: Preparation of Solid Zuclomiphene Binaphthyl Hydrogen Phosphate Salt (1-A)·(BPA)

A solution of clomiphene citrate ((1)·(citric acid), E:Z isomeric ratio 60:40, 20 g, 0.0334 mol) and racemic binaphthyl hydrogen phosphate (BPA) (12.2 g, 0.0351) in methanol (280 mL) was stirred at room temperature. The resulting suspension was heated to 50-55° C. for about five hours to afford a uniform mixture. The mixture was cooled to room temperature and stirred for about three hours prior to filtration at room temperature, washing with methanol (1×20 mL), and drying in vacuo at 40-45° C. for about 18 hours to afford solid enclomiphene binaphthyl hydrogen phosphate ((1-B)·(BPA), 14.09 g, 93.1% recovery of available). The solid was determined to have an isomeric ratio of enclomiphene:zuclomiphene of about 97:3 (97% isomeric purity (E)) by $^1$H NMR.

The resulting mother liquor was concentrated to about 100 mL, methyl t-butyl ether (80 mL) was added and the resulting mixture was stirred at room temperature for about 18 hours. The resulting suspension was stirred at 0-5° C. for about four hours prior to filtration and drying in vacuo at 45-50° C. to afford solid zuclomiphene binaphthyl hydrogen phosphate ((1-A)·(BPA), 7.3 g, 72.4% recovery of available). The solid was determined to have an isomeric ratio of zuclomiphene:enclomiphene of about 97:3 (97% isomeric purity (Z)) by $^1$H NMR.

Example 4: Preparation of Solid Zuclomiphene Citrate (1-A)·(Citric Acid)

A thick slurry of zuclomiphene binaphthyl hydrogen phosphate ((1-A)·(BPA), 5 g, 0.0066 mol, 97.2% isomeric purity (Z) by $^1$H NMR), ethyl acetate (50 mL), solid potassium carbonate (1.05 g, 0.0076 mol) and water (1 mL) was stirred at room temperature for about 21 hours to afford a free flowing slurry. The slurry was filtered and the solid was washed with ethyl acetate (2×10 mL). The filtrate was washed with potassium carbonate solution (25 mL), water (25 mL) and brine (25 mL). A solution of citric acid (1.20 g, 0.0063 mol) in methanol (5 mL) was added and the resulting slurry was heated to 55-60° C. for 2 hours, then cooled to 0-5° C. for about 4 hours and filtered. The solid was collected by filtration, washed with ethyl acetate (2×10 mL) and dried in vacuo at 45-50° C. to afford zuclomiphene citrate ((1-A)·(citric acid), 3.22 g, 81.2% yield). The solid was determined to have an isomeric purity (Z) of 97.4% by $^1$H NMR.

$^1$H NMR of zuclomiphene citrate (1-A)·(citric acid) (CD$_3$OD, 300 MHz) δ: 1.36 (t, J=7.3 Hz, 6H), 2.76 (Abq, J$^{1-2}$=15.4 Hz, J$^{1-3}$=28.6 Hz, 4H) 3.40-3.2 (m, 4H+CH$_3$OH), 3.60 (t, J=4.9 Hz, 2H), 4.39 (t, J=4.9 Hz, 2H), 6.97-6.87 (m, 2H), 7.14-7.00 (m, 5H), 7.23-7.15 (m, 3H), 7.37-7.24 (m, 4H).

Example 5: Preparation of Zuclomiphene Oxalate (1-A)·(OXL)

A solution of clomiphene citrate ((1)·(citric acid) E:Z isomeric ratio 60:40, 20 g, 0.0334 mol) and racemic binaphthyl hydrogen phosphate (BPA) (12.2 g, 0.0351 mol) in methanol (240 mL) was heated to 25-35° C. for about 5 hours to afford a uniform mixture. The mixture was then filtered, washed with methanol (3×20 mL) and dried in vacuo at 40-45° C. for about 18 hours to afford solid enclomiphene binaphthyl hydrogen phosphate ((1-B)·(BPA), 14.2 g, 93.8% recovery of available). The solid was determined to have an isomeric ratio of enclomiphene:zuclomiphene of about 96:4 (96% isomeric purity (E)) by $^1$H NMR.

The resulting mother liquor was concentrated to a volume of about 100 mL (about 4 volumes in relation to the initial combined mass of enclomiphene binaphthyl hydrogen phosphate salt and zuclomiphene binaphthyl hydrogen phosphate salt (25 g calculated from citrate)), ethyl acetate (100 mL) was added and the resulting mixture was concentrated to about 100 mL. This procedure was repeated by charging ethyl acetate (100 mL) and distilling back to about 100 mL volume to essentially remove methanol. Ethyl acetate (100 mL), water (5 mL) and potassium carbonate (20.6 g, 0.1503 mol) were added and the mixture was stirred at room temperature for about 21 hours to afford a free-flowing slurry. The slurry was filtered, and the solid cake was washed with ethyl acetate (2×40 mL). The filtrate was washed with potassium carbonate solution (80 mL) and water (120 mL) and the organic layer was concentrated to near dryness. To the resulting oily material was charged ethyl acetate (60 mL), acetone (100 mL), and oxalic acid dihydrate (2.1 g, 0.0167 mol) and the mixture was stirred at room temperature for about 6 hours. The mixture was filtered, washed with a mixture (1:1) of ethyl acetate:acetone (2×10 mL), and dried in vacuo at 40-45° C. for about 18 hours to afford solid zuclomiphene oxalate ((1-A)·(OXL), 4.66 g, 70% recovery of available). The solid was determined to have an isomeric ratio of zuclomiphene:enclomiphene of about 96:4 (96% isomeric purity (Z)) by $^1$H NMR.

The solid was further purified by stirring a suspension in acetone (100 mL) at 45-50° C. for about 23 hours, cooling and stirring at room temperature for about 2 hours, filtering the solid, washing with acetone (2×10 mL) and drying in vacuo at 40-45° C. for about 18 hours to afford solid zuclomiphene oxalate ((1-A)·(OXL), 4.53 g, 67.5% recovery of available). Isomeric ratio (HPLC): 99.21% Z and 0.79% E.

Example 6: Preparation of Zuclomiphene Oxalate (1-A)·(OXL) Form APO-1

A solution of clomiphene citrate ((1)·(citric acid) E:Z isomeric ratio 60:40, 50 g, 0.0836 mol) and racemic binaphthyl hydrogen phosphate (BPA) (29 g, 0.0836) in methanol (600 mL) was heated to 25-35° C. for about 6 hours to afford a uniform mixture. The mixture was then filtered, washed with methanol (3×100 mL) and dried in vacuo at 40-45° C. for about 18 hours to afford solid enclomiphene binaphthyl hydrogen phosphate ((1-B)·(BPA), 35 g, 92.5% recovery of available). The solid was determined to have an isomeric ratio of enclomiphene:zuclomiphene of about 98:2 (98% isomeric purity (E)) by $^1$H NMR.

The resulting mother liquor was concentrated to a volume of about 250 mL (about 4 volumes in relation to the initial combined mass of enclomiphene binaphthyl hydrogen phosphate salt and zuclomiphene binaphthyl hydrogen phosphate salt (63 g calculated from citrate)), ethyl acetate (250 mL) was added and the resulting mixture was concentrated to about 250 mL. This procedure was repeated by charging ethyl acetate (250 mL) and distilling back to about 250 mL volume to essentially remove methanol. Ethyl acetate (250 mL), water (12.5 mL) and potassium carbonate (51.9 g, 0.376 mol) were added and the mixture was stirred at room temperature for about 20 hours to afford a free-flowing slurry. The slurry was filtered, and the solid cake was washed with ethyl acetate (2×100 mL). The filtrate was washed with potassium carbonate solution (200 mL) and water (300 mL) and the organic layer was concentrated to near dryness. To the resulting oily material was charged ethyl acetate (200 mL), acetone (200 mL) and oxalic acid dihydrate (5.3 g, 0.418 mol), and the mixture was stirred at about 50° C. for about 64 hours. The mixture was cooled to room temperature, filtered, washed with a mixture (1:1) of ethyl acetate:acetone (2×50 mL), and dried in vacuo at 40-45° C. for about 18 hours to afford solid zuclomiphene oxalate ((1-A)·(OXL), 12.1 g, 72.5% recovery of available). Isomeric ratio (HPLC): 99.55% Z, 0.45% E.

The solid was further purified by stirring a suspension in acetone (250 mL) at 45-50° C. for about 23 hours, cooling and stirring at room temperature for about 2 hours, filtering the solid, washing with acetone (2×25 mL) and drying in vacuo at 40-45° C. for about 18 hours to afford solid zuclomiphene oxalate Form APO-I ((1-A)·(OXL), 11.2 g, 67.5% recovery of available). Isomeric ratio (HPLC): 99.73% Z, 0.27% E. The PXRD diffractogram and DSC thermogram of a sample prepared by this method are provided in FIG. 3 and FIG. 4, respectively.

Example 7: Preparation of Zuclomiphene Oxalate (1-A)·(OXL) Form APO-II

A mixture of zuclomiphene free base (100 mg, 0.25 mmol, 94.1% isomeric purity (Z) by $^1$H NMR) and oxalic acid (23.4 mg, 0.26 mmol) in ethyl acetate (6 mL) was heated at 60° C. for 2 hours. Heating was discontinued and the mixture was allowed to cool to room temperature and stand overnight. The solvent was decanted, and the white solid was washed with heptanes to afford zuclomiphene oxalate Form APO-II ((1-A)·(OXL)). The PXRD diffractogram and DSC thermogram of a sample prepared by this method are provided in FIG. 5 and FIG. 6, respectively.

¹H NMR of zuclomiphene oxalate (1-A)·(OXL) (DMSO-d$_6$, 400 MHz): 51.20 (t, J=7.2 Hz, 6H), 3.12 (m, 4H), 3.42 (br, 2H), 4.29 (br, 2H), 6.94-7.03 (m, 4H), 7.13-7.15 (m, 3H), 7.22-7.30 (m, 7H).

Example 8: Preparation of Zuclomiphene Oxalate (1-A)·(OXL) Form APO-III

In a sealed vial, zuclomiphene oxalate (Form APO-I, 111 mg) was dissolved in acetic acid (400 μL) at 60° C. and toluene (1.50 mL) was added. The resulting solution was temperature cycled for 16 hours, over which time precipitation occurred. The solid was collected by filtration and dried in vacuo at room temperature for approximately 24 hours to afford zuclomiphene oxalate form APO-III ((1-A)·(OXL), 59 mg) as a white solid. The PXRD diffractogram and DSC thermogram of a sample prepared by this method are provided in FIG. 7 and FIG. 8, respectively.

Example 9: Preparation of Zuclomiphene Oxalate (1-A)·(OXL) Form APO-IV

In a sealed vial, zuclomiphene oxalate (Form APO-I, 110 mg) was dissolved in dimethyl sulfoxide (600 μL) at 60° C. and acetone (2.25 mL) was added. The resulting solution was temperature cycled for 16 hours, over which time precipitation occurred. The solid was collected by filtration and dried in vacuo at room temperature for approximately 24 hours to afford zuclomiphene oxalate Form APO-IV ((1-A)·(OXL), 33 mg) as a white solid. The PXRD diffractogram and DSC thermogram of a sample prepared by this method are provided in FIG. 9 and FIG. 10, respectively.

What is claimed is:

1. A process for the preparation of a solid that is isomerically enriched in zuclomiphene of Formula (1-A) relative to enclomiphene of Formula (1-B):

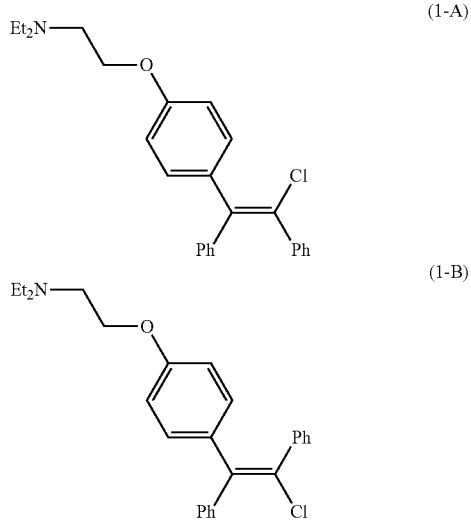

or a salt thereof, the process comprising:
  (i) crystallizing and isolating a solid, from a mixture comprising enclomiphene binaphthyl hydrogen phosphate salt and zuclomiphene binaphthyl hydrogen phosphate salt in a solvent (S1), that is isomerically enriched in the enclomiphene binaphthyl hydrogen phosphate salt to afford a first solution;

and either:
  (ii-a) crystallizing and isolating a solid from the first solution that is isomerically enriched in the zuclomiphene binaphthyl hydrogen phosphate salt; or
  (ii-b)(a) treating the first solution with a base to liberate binaphthyl phosphate salt and removing it from the first solution to afford a second solution;
    (b) treating the second solution with oxalic acid; and
    (c) crystallizing and isolating a solid from the second solution that is isomerically enriched in the zuclomiphene oxalate salt;

wherein the mixture is enriched in enclomiphene binaphthyl hydrogen phosphate salt relative to zuclomiphene binaphthyl hydrogen phosphate salt.

2. The process of claim 1, wherein step (i) comprises combining a composition comprising zuclomiphene and enclomiphene, or a composition comprising salts thereof, with binaphthyl hydrogen phosphate in a solvent (S1) and maintaining the mixture at a suitable temperature for a suitable time.

3. The process of claim 2, wherein the composition comprises zuclomiphene citrate and enclomiphene citrate.

4. The process of claim 1, wherein the solvent (S1) is methanol.

5. The process of claim 1, wherein the process comprises steps (ii-b)(a), (ii-b)(b), and (ii-b)(c).

6. The process of claim 5, wherein the base is solid potassium carbonate.

7. The process of claim 5, wherein solid potassium binaphthyl phosphate salt is generated and is removed from the first solution by filtration.

8. The process of claim 5, wherein solvent (S1) is methanol and step (ii-b)(a) comprises replacing a portion of the methanol with ethyl acetate and water such that the solvent composition comprises, with respect to ethyl acetate, about 10-15 mole % water and less than about 20 mole % methanol, prior to filtration.

9. The process of claim 1, wherein the zuclomiphene binaphthyl hydrogen phosphate salt or the zuclomiphene oxalate salt that is isolated is further converted to zuclomiphene citrate salt.

* * * * *